United States Patent
Edwards et al.

(10) Patent No.: US 6,733,515 B1
(45) Date of Patent: *May 11, 2004

(54) UNIVERSAL INTRODUCER

(75) Inventors: Stuart D. Edwards, Portola Valley, CA (US); Ronald Lax, Palm City, FL (US); Theodore L. Parker, Danville, CA (US); Thomas C. Wehman, Cupertino, CA (US); Theodore Kucklick, Los Gatos, CA (US)

(73) Assignee: NeoMend, Inc., Rancho Santa Margarita, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/037,659

(22) Filed: Mar. 10, 1998

Related U.S. Application Data

(63) Continuation-in-part of application No. 08/963,408, filed on Nov. 3, 1997, now Pat. No. 6,033,401.
(60) Provisional application No. 60/036,299, filed on Mar. 12, 1997.

(51) Int. Cl.$^7$ .............................. A61D 1/00; A61M 5/00
(52) U.S. Cl. ........................ 606/214; 606/213; 604/264
(58) Field of Search ............................. 604/20, 21, 41, 604/278, 501, 506, 507, 508, 48, 93.01, 113, 114, 158, 164.01, 181, 187, 218, 264, 523; 606/213, 214–215, 32–33, 27–31; 607/96–102, 115, 154

(56) References Cited

U.S. PATENT DOCUMENTS

| | | |
|---|---|---|
| 4,424,833 A | 1/1984 | Spector et al. |
| 4,555,242 A | 11/1985 | Saudager |
| 4,738,658 A | 4/1988 | Magro et al. |

(List continued on next page.)

FOREIGN PATENT DOCUMENTS

| | | |
|---|---|---|
| EP | 0 330 344 | 2/1988 |
| EP | 0 476 178 A1 | 3/1992 |
| EP | 0 482 350 A2 | 4/1992 |
| EP | 0 482 350 B1 | 12/1996 |
| GB | 1 569 660 | 7/1977 |
| WO | 91/09641 | 7/1991 |
| WO | 92/22252 | 12/1992 |

OTHER PUBLICATIONS

Vascular Solutions, Inc., Products Web Pages. www.vascularsolutions.com Nov. 12, 2003.*

(List continued on next page.)

*Primary Examiner*—Brian L. Casler
*Assistant Examiner*—Catherine S. Williams
(74) *Attorney, Agent, or Firm*—Ryan Kromholz & Manion, S.C.

(57) ABSTRACT

A device for introducing a catheter into a vessel through a puncture in a vessel and for sealing the puncture. The device includes an elongated body having a proximal end and a distal end sized to be positioned within a tissue site which includes the puncture. The elongated body includes a utility lumen sized to allow a catheter to be delivered through the utility lumen. The utility lumen is positioned within the elongated body so positioning the elongated body within the tissue site allows a catheter delivered through the utility lumen to enter the vessel. The elongated body also includes a closure lumen having an entrance port. A closure composition can be delivered through the entrance port into the closure lumen. The closure lumen also includes an exit port adjacent the distal end of the elongated body. The closure composition delivered into the closure lumen can be delivered through the exit port to the tissue site adjacent the puncture.

25 Claims, 30 Drawing Sheets

U.S. PATENT DOCUMENTS

| | | | | |
|---|---|---|---|---|
| 4,744,364 | A | 5/1988 | Kensey | 128/334 R |
| 4,838,280 | A | 6/1989 | Haaga | 128/751 |
| 4,852,568 | A | 8/1989 | Kensey | |
| 4,874,368 | A | 10/1989 | Miller et al. | |
| 4,890,612 | A | 1/1990 | Kensey | |
| 4,891,359 | A | 1/1990 | Saferstein et al. | |
| 5,002,051 | A | 3/1991 | Dew et al. | |
| 5,021,059 | A | 6/1991 | Kensey et al. | |
| 5,041,129 | A | 8/1991 | Hayhurst et al. | 606/232 |
| 5,042,985 | A | 8/1991 | Elliott et al. | |
| 5,053,046 | A | 10/1991 | Janese | |
| 5,061,274 | A | 10/1991 | Kensey | |
| 5,108,421 | A | 4/1992 | Fowler | |
| 5,129,882 | A | 7/1992 | Weldon et al. | |
| 5,156,613 | A | 10/1992 | Sawyer | |
| 5,159,937 | A | 11/1992 | Tremulis | |
| 5,163,906 | A | 11/1992 | Ahmadi | |
| 5,171,222 | A | 12/1992 | Euteneuer et al. | |
| 5,192,300 | A | 3/1993 | Fowler | |
| 5,197,971 | A | 3/1993 | Bonutti | 606/192 |
| 5,221,259 | A | 6/1993 | Weldon et al. | |
| 5,222,974 | A | 6/1993 | Kensey et al. | |
| 5,250,025 | A | 10/1993 | Sosnowski et al. | |
| 5,275,616 | A | 1/1994 | Fowler | |
| 5,281,197 | A | 1/1994 | Arias et al. | 604/57 |
| 5,282,827 | A | 2/1994 | Kensey et al. | |
| 5,290,310 | A | 3/1994 | Makower et al. | 606/213 |
| 5,292,309 | A | 3/1994 | Van Tassel et al. | |
| 5,292,332 | A | 3/1994 | Lee | |
| 5,306,254 | A | 4/1994 | Nash et al. | |
| 5,324,306 | A | 6/1994 | Makower et al. | 606/213 |
| 5,383,896 | A | * 1/1995 | Gershony et al. | 606/213 |
| 5,411,520 | A | 5/1995 | Nash et al. | |
| 5,413,571 | A | 5/1995 | Katsaros et al. | |
| 5,415,657 | A | 5/1995 | Taymor-Luria | |
| 5,419,765 | A | 5/1995 | Weldon et al. | 604/96 |
| 5,437,292 | A | 8/1995 | Kipshidze et al. | 128/898 |
| 5,441,517 | A | * 8/1995 | Kensey et al. | 128/887 |
| 5,447,502 | A | 9/1995 | Haaga | 604/265 |
| 5,486,195 | A | 1/1996 | Myers et al. | |
| 5,496,332 | A | 3/1996 | Sierra et al. | 606/139 |
| 5,507,744 | A | * 4/1996 | Tay et al. | 606/50 |
| 5,571,216 | A | 11/1996 | Anderson | |
| 5,575,815 | A | 11/1996 | Slepian et al. | |
| 5,591,204 | A | 1/1997 | Janzen et al. | |
| 5,591,205 | A | 1/1997 | Fowler | |
| 5,601,602 | A | 2/1997 | Fowler et al. | |
| 5,612,050 | A | 3/1997 | Rowe et al. | |
| 5,626,601 | A | * 5/1997 | Gershony et al. | 606/194 |
| 5,630,833 | A | 5/1997 | Katsaros et al. | 606/213 |
| 5,649,959 | A | * 7/1997 | Hannam et al. | 604/181 |
| 5,653,730 | A | * 8/1997 | Hammerslag | 606/214 |
| 5,665,106 | A | 9/1997 | Hammerslag | 606/214 |
| 5,665,107 | A | 9/1997 | Hammerslag | 606/214 |
| 5,669,934 | A | 9/1997 | Sawyer | 606/213 |
| 5,676,689 | A | 10/1997 | Kensey et al. | |
| 5,700,273 | A | 12/1997 | Buelna et al. | 606/148 |
| 5,725,498 | A | 3/1998 | Janzen et al. | 604/51 |
| 5,725,551 | A | 3/1998 | Myers et al. | |
| 5,728,132 | A | * 3/1998 | Van Tassel | 606/213 |
| 5,810,810 | A | * 9/1998 | Tay et al. | 606/50 |
| 5,814,008 | A | * 9/1998 | Chen et al. | 604/21 |
| 5,951,583 | A | * 9/1999 | Jensen et al. | 606/194 |
| 6,033,401 | A | * 3/2000 | Edwards et al. | 606/41 |

OTHER PUBLICATIONS

Vascular Solutions, Inc. Products, www.vascularsolutions.com, information on site Nov. 12, 2003.

Abergelm R. P., et al. "Skin closure by Nd:YAG laser welding." *American Academy of Dermatology*. 1986. 14(5):810–14.

Anand, R. K., et al. "Laser Balloon Angioplasty: Effect of Constant Temperature Versus Constant Power on Tissue Weld Strength." *Lasers in Surgery and Medicaine*. 1988. 8(1):40–44.

Chuck, R. S., et al. "Dye–Enhanced Laser Tissue Welding." *Lasers in Surgery and Medicine*. 1989. 9(5):471–477.

DeCoste, S. D., et al. "Dye–Enhanced Laser Welding for Skin Closure." *Lasers in Surgery and Medicine*. 1992. 12:25–32.

Fujitani, R. M., et al. "Biophysical Mechanisms of Argon Laser–Assisted Vascular Anastomoses." *Current Surgery*. Mar.–Apr. 1998. p119–123.

Goldstein, J. D., et al. "Development of a Reconstituted Collagen Tendon Proshesis." *The Journal of Bone and Joint Surgery*. 1989. 71–A(8):1183–91.

Grubbs, P. E., et al. "Enhanccement of $CO_2$ Laser Microvascular Anastomoses by Fibrin Glue." *Journal of Surgical Research*. 1988. 45:112–119.

Grubbs, P. E., et al. "Determinants of Weld Strength in Laser–Assisted Microvascular Anastomosis." *Current Surgery*. Jan.–Feb. 1989. p. 3–5.

Jain, K. K., et al. "Repair of small blood vessels with the Neodymium–YAG laser: A preliminary report." *Surgery*. 85(6):684–8.

Kopchok, G., et al. "Thermal Studies on In–Vivo Vascular Tissue Rusion by Argon Laser." *Journal of Investigative Surgery*. 1988. 1:5–12.

Kopchok, G., et al. "Argon laser vascular welding: he thermal component." *SPIE*. 1986. 712:260–3.

Kopchok, G. E., et al. "$CO_2$ and Argon Laser Veascular Welding: Acute Histologic and Thermodynamic Comparison." *Lasers in Surgery and Medicine*. 1988. 8:584–8.

Lemole, G. M., et al. "Preliminary evaluation of collagen as a componenet in the thermally–induced 'weld'." *SPIE*. 1991. 1422:116–22.

Mininberg, D. T., et al. "Laser welding of perdicled flap skin tubes." *The Journal or Urology*. 1989. 142(2):623–5.

Murray, L. W., et al. "Crosslinking of Extracellular Matrix Proteins." *Lasers in Surgery and Medicine*. 1989. 9:490–6.

Nimni, M. E. "Third International Congress of Biorthology Symposium on he Soft Tissues Around a Diarthrodial Joint." *Biorheology*. 1980. 17:51–82.

Oz, M. C., et al. "Tissue soldering by use of indocyanine green dye–enhanced fibrinogen with the near infrared diode laser." *Journal of Vascular Surgery*. 1990. 11(5):718–25.

Oz, M. C., et al. "In Vitro Comparison of Thulium–Holmium–Chromium–YAG and Argon Ion Lasers for Welding of Biliary Tissue." *Lasers in Surgery and Medicine*. 1989. 9:248–53.

Gilbert, P. T., et al. "Laser–Assisted Vasovasostomy." 1989. 9:42–44.

Poppas, D. P., et al. "Laser Welding in Urethral Surgery: Improved Results with a Protein Solder." *The Journal of Urology*. 1988. 139:415–17.

Schober, R., et al. "Laser–Induced Alteration of Collagen Substructure Allows Microsurgical Tissue Welding." *Science*. Jun. 1986. 232:1421–2.

Tanzer, M. L., et al. "Cross–Linking of Collagen." *Science.* 180:561–6.

Vale, B. H., et al. "Microsurgical Anastomosis of Rat Carotid Arteries with the $CO_2$ Laser." *Plastic and Reconstructive Surgery.* 77(5):759–66.

White, R. A., et al. "Argon laser—welded arteriovenous anastomoses." *Journal of Vascular Surgery.* 1987. 6(5):447–53.

White, R. A., et al. "Comparison of Laser–Welded and Sutered Arteriotomies." *Arch Surg.* 1986. 121:1133–5.

White, R. A., et al. "Mechanism of Tissue Fusion in Argon Laser–Welded Vein–Artery Anastomoses." *Lasers in Surgery and Medicine.* 1988. 8:83–9.

* cited by examiner

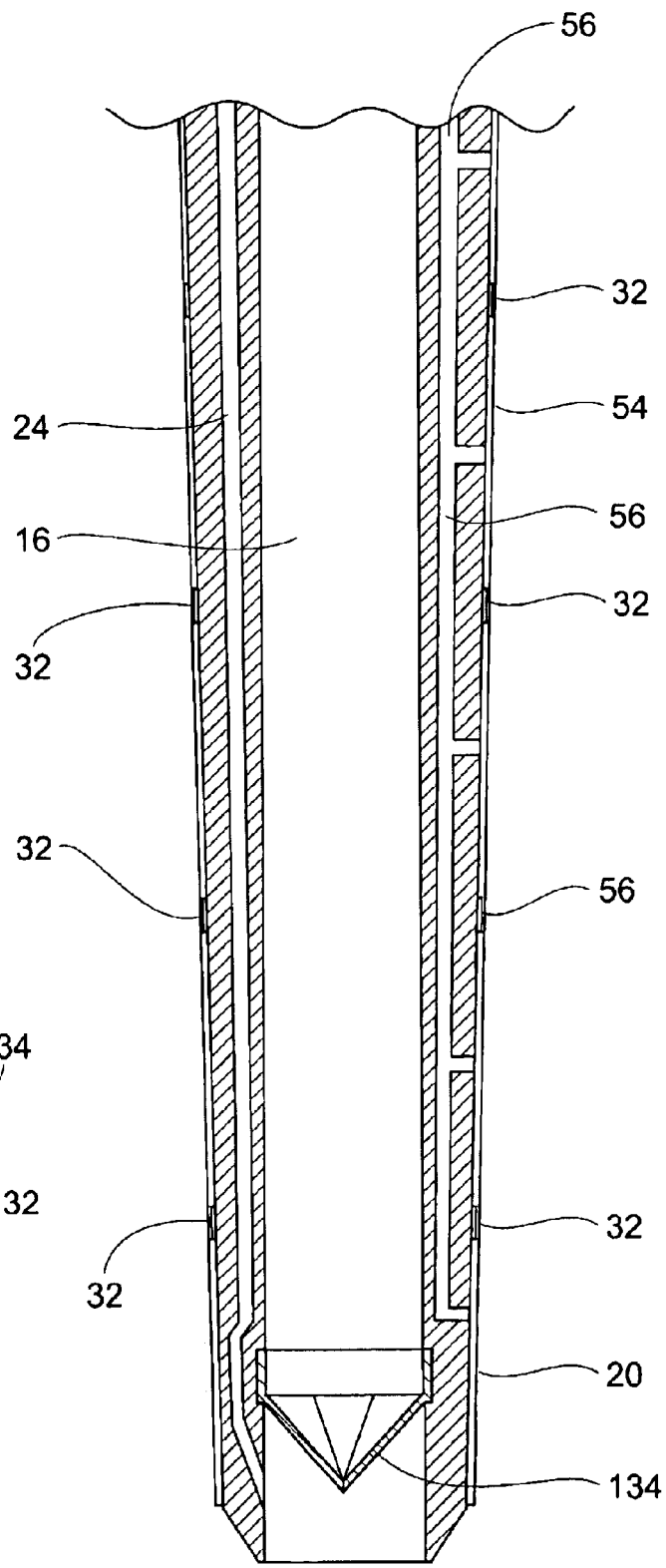
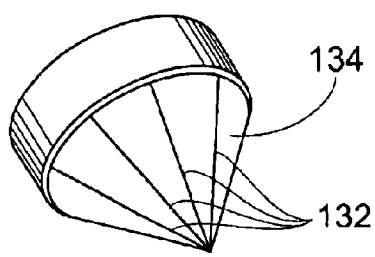
Fig. 17
Fig. 18

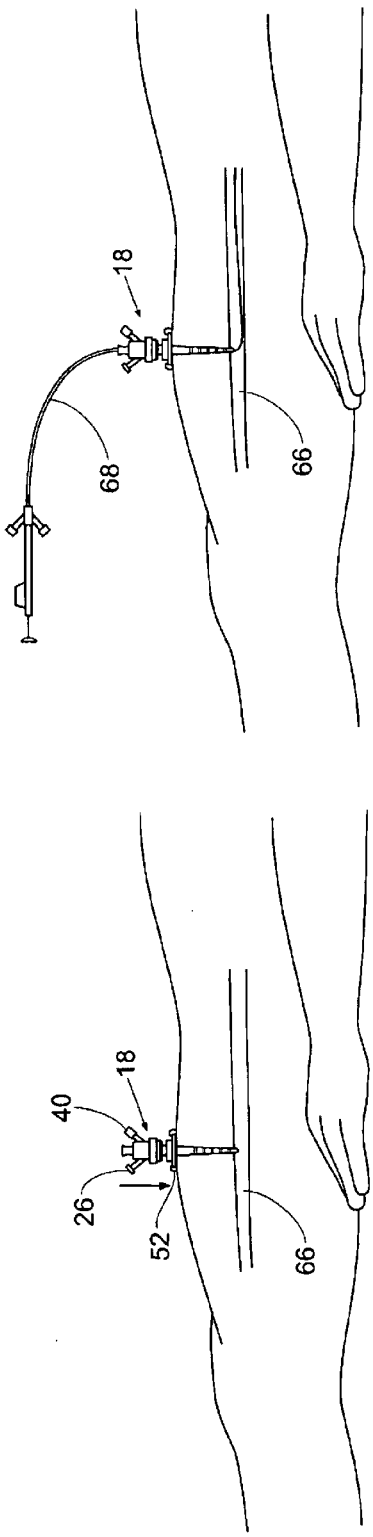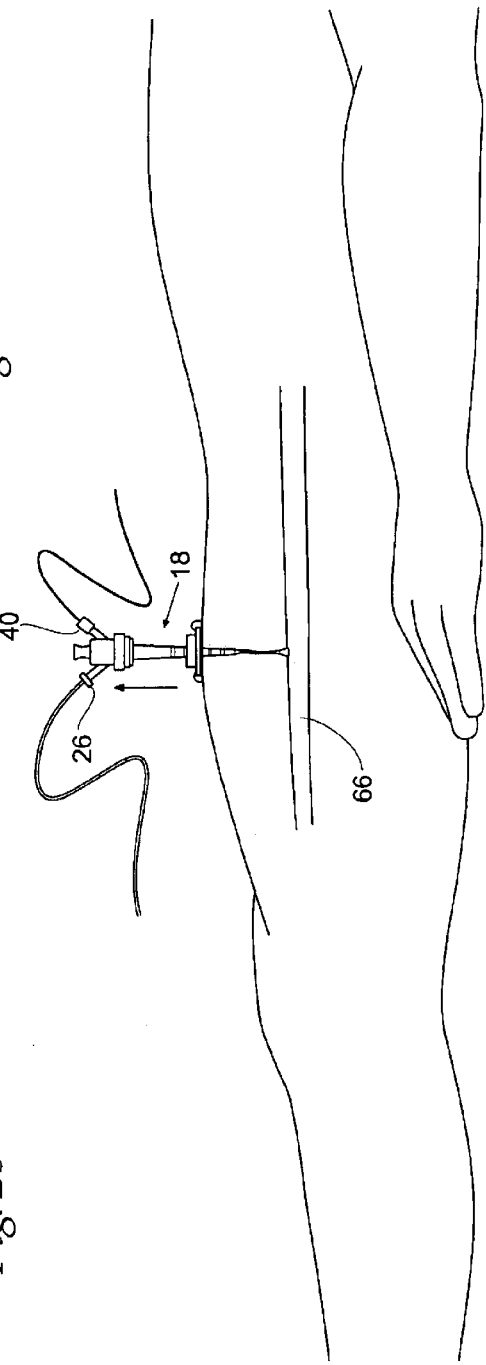
Fig. 20
Fig. 21
Fig. 22

UNIVERSAL INTRODUCER

RELATIONSHIP TO COPENDING APPLICATION

This application claims the benefit of Provisional U.S. Application Serial No.: 60/036,299, Filed: Mar. 12, 1997, entitled "Universal Introducer", which is incorporated herein by reference. This application is also a continuation-in-part of U.S. application Ser. No.08/963,408, filed Nov. 3, 1997, and entitled "Vascular Sealing Device with Microwave Antenna," now U.S. Pat. No. 6,033,401.

FIELD OF THE INVENTION

This invention relates to a wound closure device, and more particularly to a device for delivering a catheter to a vessel within a tissue site and closing a wound caused by the catheter delivery.

BACKGROUND OF THE INVENTION

A wide variety of surgical procedures are performed by introducing a catheter into a vessel. After the surgical procedure is completed, closure of the vessel at the site where the catheter was introduced is needed. Vessel punctures formed in the process of performing a catheter based surgical procedure are commonly 1.5 mm to 7.0 mm in diameter and can be larger. Closure of these punctures is frequently complicated by anticoagulation medicine given to the patient which interferes with the body's natural clotting abilities.

Closure of a vessel puncture has traditionally been performed by applying pressure to the vessel adjacent the puncture site. This procedure requires the continuous attention of at least one medical staff member to apply pressure to the vessel puncture site and can take as long as 30 minutes.

Devices have been developed for effecting the closure of vessel punctures through the application of energy. See U.S. Pat. Nos. 5,626,601; 5,507,744; 5,415,657; and 5,002,051. Devices have also been developed for effecting the closure of vessel punctures through the delivery of a mechanical mechanism which mechanically seals the puncture. See U.S. Pat. Nos.: 5,441,520; 5,441,517; 5,306,254; 5,282,827; and 5,222,974. Devices have also been developed for effecting the closure of vessel punctures through the delivery of a composition to block the vessel puncture. See U.S. Pat. Nos. 5,601,602; 5,591,205; 5,441,517; 5,292,332; 5,275,616; 5,192,300; and 5,156,613. Despite the various devices that have been developed for closing vessel punctures, a need still exists for a single device which can be used for both introducing a catheter into a vessel and for closing the resulting wound.

SUMMARY OF THE INVENTION

The invention relates to a device for introducing a catheter through a puncture in a vessel and for sealing the puncture. The device includes an elongated body having a proximal end and a distal end sized to be positioned within a tissue site which includes the puncture. The elongated body includes a utility lumen sized to allow delivery of a catheter through the utility lumen. The utility lumen is positioned within the elongated body so positioning the elongated body within the tissue site allows a catheter delivered through the utility lumen to enter the vessel. The elongated body also includes a closure lumen having an entrance port. A closure composition can be delivered through the entrance port into the closure lumen. The closure lumen also includes an exit port adjacent the distal end of the elongated body. The closure composition delivered into the closure lumen can be delivered through the exit port to the tissue site adjacent the puncture.

The invention also relates to a device for introducing a catheter through a puncture in a vessel and for sealing tissues adjacent the puncture. The device includes an elongated body having a proximal end and a distal end sized to be positioned within a tissue site which includes the puncture. A membrane is included at an outer surface of the elongated body. The membrane is positioned on the elongated body so the membrane is adjacent a portion of the tissue adjacent the puncture when the elongated body is positioned within the tissue site. The membrane is sufficiently porous to allow a closure composition to pass through the membrane. The closure composition can be delivered into the closure lumen through an entrance port. The closure composition can be delivered from the closure lumen to the membrane through at least one exit port.

The invention also relates to a system for introducing a catheter through a puncture within a vessel and sealing the puncture. The device includes an elongated body having a proximal end and a distal end sized to be positioned within a tissue site which includes the puncture. The elongated body includes a utility lumen within the elongated body. The utility lumen is sized to allow delivery of a catheter through the utility lumen. The utility lumen is positioned within the elongated body so when the elongated body is positioned within the tissue site a catheter delivered through the utility lumen can enter the vessel. A first closure lumen is coupled with the utility lumen. A closure composition can be delivered into the first closure lumen through an entrance port. The closure composition can be delivered from the first closure lumen to the utility lumen through an exit port. The system also includes an obturator with a structure which allows the obturator to be at least partially positioned in the utility lumen. Positioning the obturator within the utility lumen causes a second closure lumen to be formed. The second closure lumen is at least partially defined by the obturator and the utility lumen. The second closure lumen receives the closure composition delivered from the first closure lumen to the utility lumen and is configured to deliver the received closure compound to the tissue site.

The invention also relates to a system for introducing a catheter through a puncture within a vessel and for sealing the puncture. The system includes an elongated body having a proximal end and a distal end sized to be positioned at a tissue site which includes the puncture. The elongated body includes a utility lumen and a closure lumen through which a closure composition can be delivered to tissue at the tissue site. The system also includes a catheter guide obturator configured to be positioned within the utility lumen of the elongated body. The catheter guide obturator includes a utility lumen. The utility lumen is sized to permit delivery of a catheter through the utility lumen. The utility lumen has a geometry which permits a catheter delivered through the utility lumen to enter the vessel when the catheter guide obturator is positioned within the utility lumen of the elongated body which is positioned at the tissue site.

The invention also relates to a system for introducing a catheter through a puncture within a vessel and for sealing the puncture. The system includes an elongated body having a proximal end and a distal end sized to be positioned at a tissue site which includes the puncture. The elongated body includes a utility lumen and a closure lumen through which a closure composition can be delivered to tissue at the tissue site. The invention also includes a trocar configured to be positioned within the utility lumen, the trocar includes a sharpened tip configured to puncture the tissue making up the tissue site.

The invention also relates to a system for introducing a catheter through a puncture within a vessel and for sealing the puncture. The system includes an elongated body having a proximal end and a distal end sized to be positioned at a tissue site which includes the puncture. The elongated body includes a utility lumen and a closure lumen through which a closure composition can be delivered to tissue at the tissue site. The system also includes a sealing mold configured to be positioned within the utility lumen. The sealing mold has a structure which causes a cavity to be formed at the distal end of the elongated body when the sealing mold is positioned within the utility lumen. Closure composition delivered through the closure lumen is delivered into the cavity.

The invention also relates to a method for introducing a catheter through a puncture within a vessel and for sealing the puncture. The method is initiated by providing a device with an elongated body configured to be positioned within a tissue site. The body includes a utility lumen sized to accommodate a catheter and at least one closure lumen. A closure composition can be delivered through the closure lumen. The method concludes by positioning the elongated body within the tissue site; delivering a catheter through the utility lumen into the vessel; performing a treatment with the catheter; withdrawing the catheter through the utility lumen; and delivering a closure composition through the closure lumen to the puncture.

BRIEF DESCRIPTION OF THE FIGURES

FIG. 17 is a cross section of a distal portion of a closure device.

FIG. 18 is a sideview of a flapper valve.

FIG. 20 illustrates an closure device held within a tissue site by sutures.

FIG. 21 illustrates a closure device in place within a tissue site. The closure device includes a catheter delivered through a utility lumen to a vessel in the tissue site.

FIG. 22 illustrates the closure device of FIG. 21 being withdrawn from tissue.

DETAILED DESCRIPTION OF THE PREFERRED EMBODIMENT

Figures 1A, 1B:
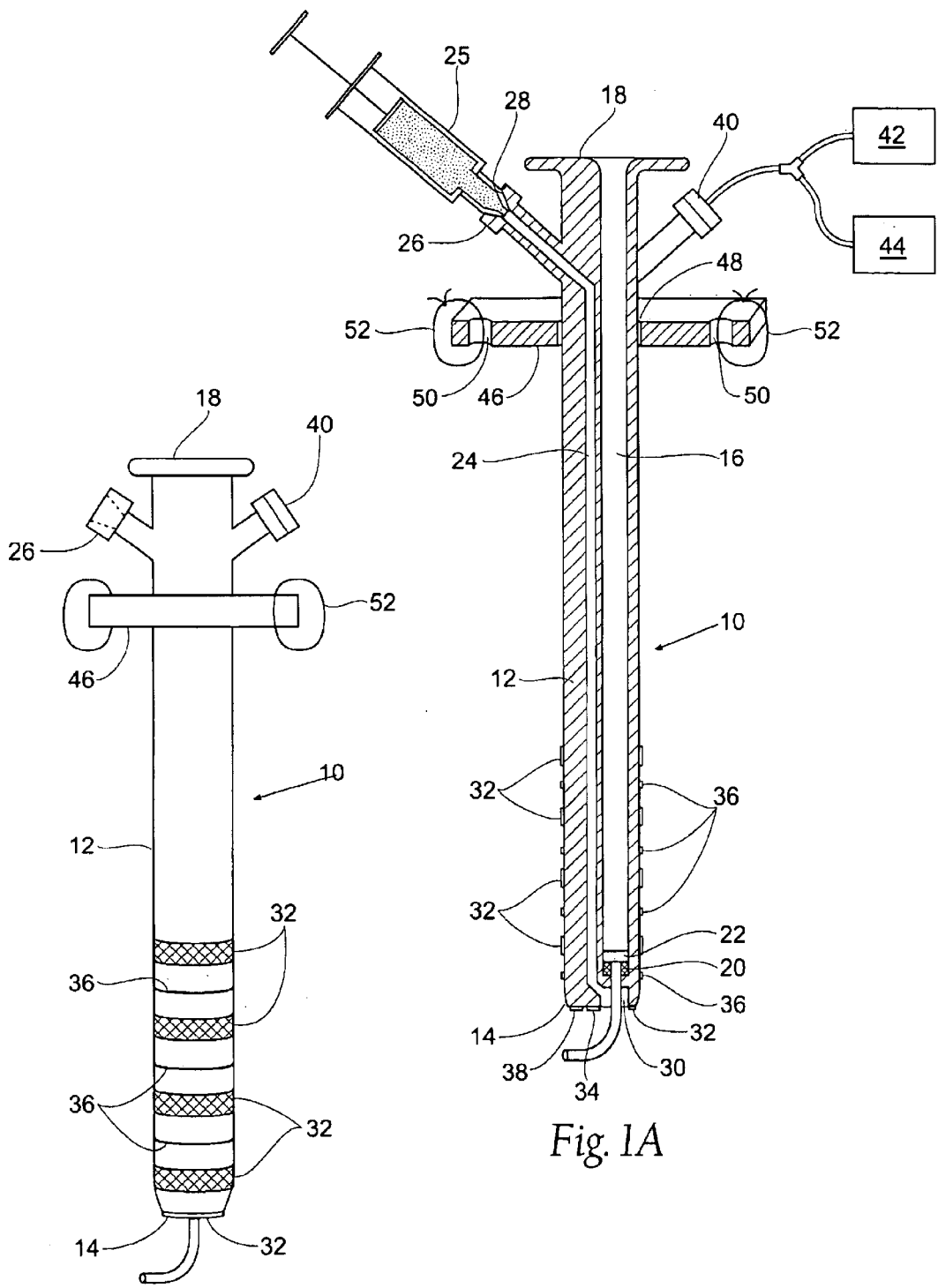
FIG. 1A is a cross section of a closure device including a closure lumen and a utility lumen.
FIG. 1B is a sideview of a closure device according to the present invention.

The present invention relates to a device and method for introducing a catheter into a vessel which is positioned within a tissue site. An embodiment of the includes a body with a proximal end and a distal end which is designed to be positioned adjacent a puncture in the vessel. The body includes a utility lumen configured so a catheter can be delivered through the utility lumen and the puncture into the vessel. The body can also include a closure lumen which can be coupled with a source of fluent closure composition. The closure composition can be delivered through the closure lumen to the puncture.

The invention can also relate to a method for using the device. The device is positioned within a tissue site so the distal end of the device is adjacent a puncture in a vessel. A catheter is passed through the utility lumen and into the vessel so a surgical procedure can be performed using the catheter. The catheter is withdrawn and a closure composition source is coupled with the closure lumen. The closure composition is delivered from the closure composition source through the closure lumen to the puncture where it serves to bind and seal the puncture. Since the device can be used for delivery of the catheter and sealing the puncture, there is no need to switch devices in the tissue site. As a result, one advantage of the present invention is a device and method which reduces the number of necessary instruments and accordingly the opportunity for infection.

The device can include an energy delivery device at the distal end of the body. The energy delivery device can deliver energy to the tissue site and closure composition which has been delivered to the puncture. The energy can serve to increase the polymerization/cure rate of the closure composition.

Additionally, application of energy to the tissue can promote coagulation and the natural healing processes of the tissues within the tissue site. The combination of these factors can increase the rate the puncture is sealed. As a result, the device can be used to effect quick closure of a vessel puncture.

The device can include a microporous membrane around the outside of the body. A closure composition source can be coupled with a second closure lumen which opens to the microporous membrane. The closure composition can be delivered through the second closure lumen and through the microporous membrane. The microporous membrane provides resistance to the passage of the closure composition and can cause the closure composition to spread out over the microporous membrane. As a result, the closure composition contacts at least a portion of the tissues adjacent the puncture. Withdrawal of the device allows these tissues to contact one another and be bound together by the closure composition. As a result, an embodiment of the device can close the tissues adjacent the puncture.

The device can also include energy delivery devices positioned at the sides of the body. When closure composition is delivered through a microporous membrane closure composition will be delivered to tissues adjacent the puncture. The side electrodes can deliver energy to closure composition which has been delivered to these tissues. The energy can increases the polymerization/cure rate of the delivered closure composition. As a result, an embodiment of the device can promote rapid closure of tissues adjacent the puncture.

The device can also include temperature sensors positioned along the body. The temperature sensors can detect the temperature of the tissues adjacent to the puncture. The signal from the temperature sensors can be fed to a control unit. The control unit can include logic which controls the flow of energy from the electrode in response to the temperature of the tissue. For instance, the flow of energy from the electrodes can be reduced when the temperature of the tissue becomes excessively elevated. As a result, an embodiment of the device can be used to reduce damage to tissues within the tissue site.

FIG. 1A illustrates a device according to the present invention. The device may be used to introduce a catheter into a vessel through a puncture in the vessel. The device can also be used to seal the puncture and close the tissues adjacent the puncture. It should be noted that the functioning of the device to close a puncture in a vessel and to close the tissues adjacent the puncture are intended to be two separate functionalities of the device which may both be incorporated into the device. Alternatively, each function may be independently incorporated into a single device of the present invention.

The device includes a body 10 for positioning within tissue. The body has lateral sides 12 which terminate in a distal end 14. The body 10 includes a utility lumen 16 through which a catheter (not shown) may be introduced at a proximal end of the device 18 and out through the distal end 14 of the device. Included adjacent the distal end 14 of the utility lumen 16 is a backflow valve 20 which reduces blood flow from the vessel through the utility lumen 16.

Positioned within utility lumen 16 is a pigtail 22 which is movable within the utility lumen 16. The pigtail 22 can pass through the device distal end 14 upon deployment and into the vessel (not shown).

The body 10 of the device also includes a closure lumen 24 for the introduction of a closure composition. The device may be connected to a closure composition source 25 by a closure composition port 26 coupled with the closure lumen 24. The closure composition port 26 is illustrated as having an internal taper 28 of a configuration to accept a luer type fluid fitting. The distal end 14 can include a reservoir 30. The closure composition can pass from the closure composition source through the closure lumen 24 into the reservoir 30.

The device can also include an electrode 32 adjacent the distal end 14 as well as side electrodes 32 adjacent the lateral sides 12 of the device. The device can optionally include an ultrasound transducer 34 adjacent the distal end 14 of the device. In addition, the device can include temperature sensors 36 as well as blood pressure sensors 38. The device includes a controls attachment port 40 in energy communication with the distal and lateral electrodes or the transducer. Similarly, the electrical attachment port can be in communication with any sensors included on the device. As a result, an energy source 42 and device control unit 44 can be coupled with the device through the controls attachment port 40. The energy source 42 can communicate energy to the electrodes. Optionally, the control unit can include logic which controls the amount of energy delivered from the energy source 42 in response to the signal provided from the sensors.

The electrodes can have several configurations including, but not limited to, ring electrodes encircling the body of the device (FIG. 1B) or positioned at the distal end of the device (FIG. 1B), electrodes which run the length of the body or electrodes which act as point sources distributed about the body of the device.

The device can include a baseplate 46 including a hole 48 through which the device may be passed. The body of the device is movable axially along the baseplate 46. The adjustability provided by the movable baseplate is useful for accommodating variations in the length of device that is required to reach the artery as is dictated by the variations in human anatomy. The baseplate 46 can also includes openings 50. Sutures 52 can be placed through the openings 50 to attach the baseplate 46 to the skin of a tissue site. Attaching the baseplate to the skin can stabilize and fix the baseplate in the position selected by the physician.

Other acceptable methods of attaching the baseplate 46 may include use of certain adhesives, particularly pressure sensitive materials.

Figure 2:
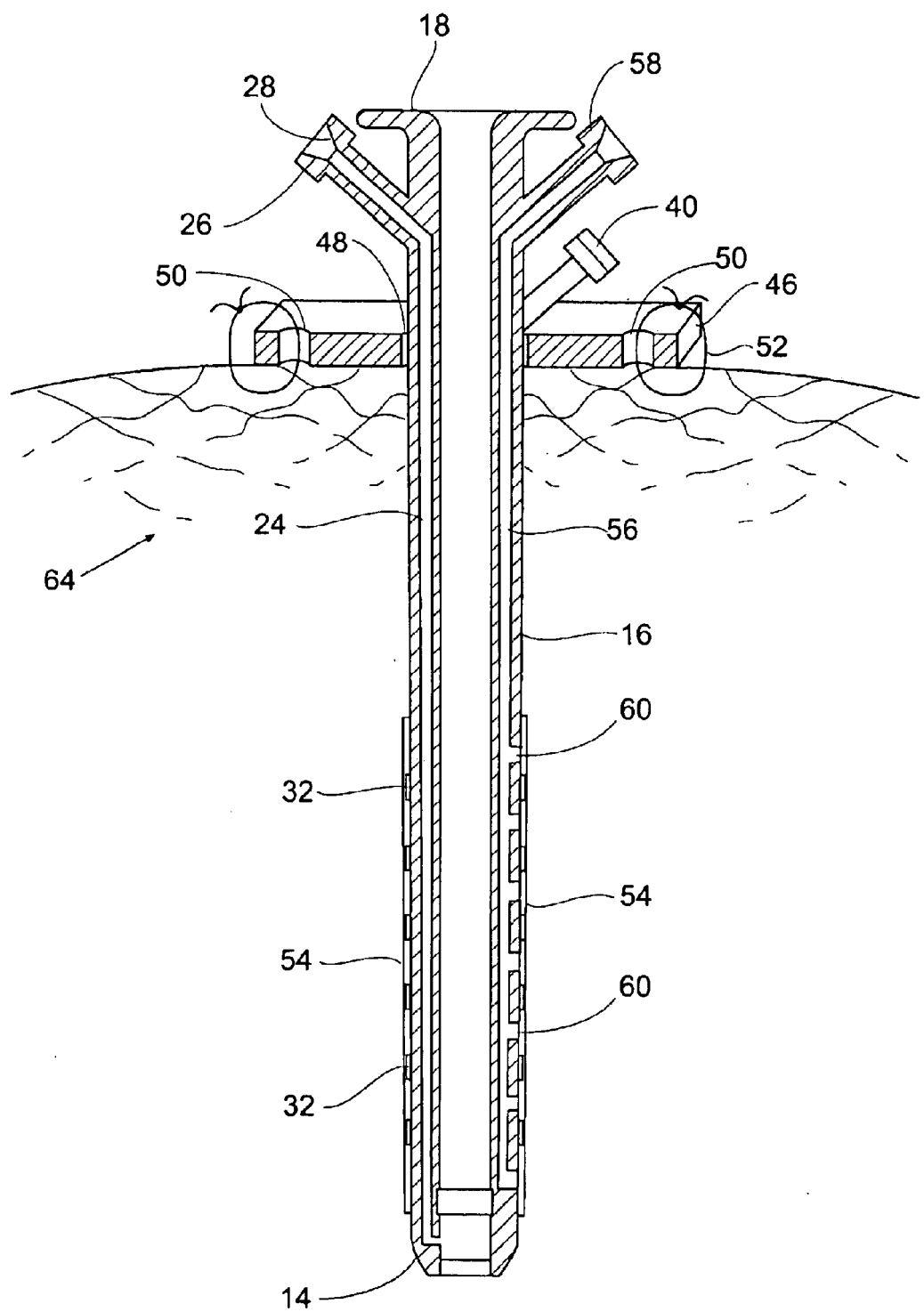
FIG. 2 is a cross section of a closure device including sensors and energy delivery devices.

FIG. 2 illustrates a device which may be used to effect the closure of a wound in a tissue site. The device includes a body 10 with a distal end 14. Lining the lateral sides 12 of the device is a microporous membrane 54 having a pore size of about 1–5,000 μm through which sealing media can be transmitted. The device includes electrodes 32 and sensors 36. The electrodes 32 and sensors 36 can be positioned between the membrane and the body or over the membrane 54.

The body 10 includes a second closure lumen 56 coupled to a second closure composition port 58. The second closure composition port 58 can be coupled to a source (not shown) for a second closure composition. The second closure lumen 56 includes a plurality of channels 60 which permit the second closure composition to pass from the second closure lumen 56 to the microporous membrane 54.

Figure 3:
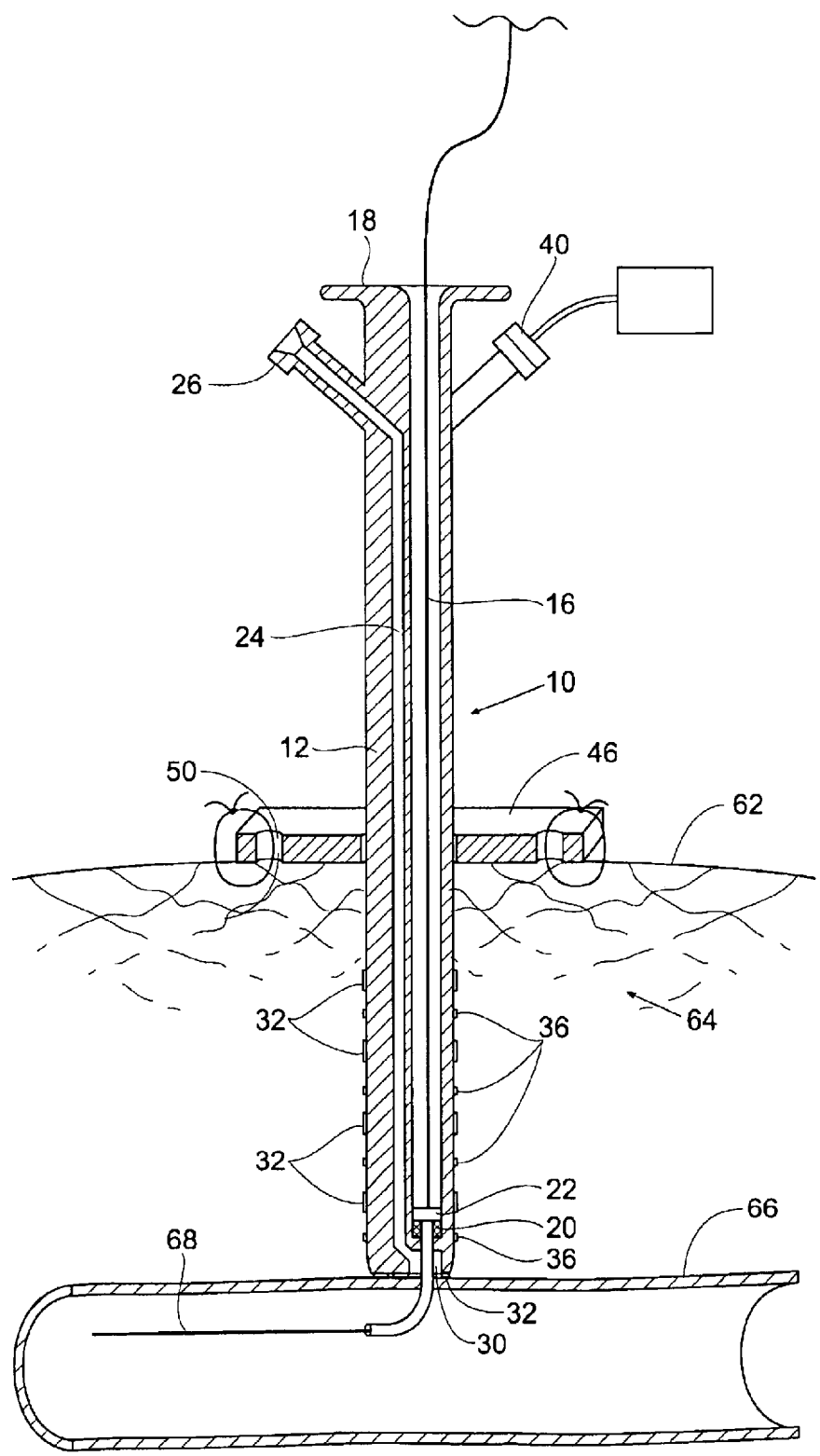
FIG. 3 is a cross section of a closure device positioned in a tissue site. The closure device includes a catheter delivered through a utility lumen to a vessel in the tissue site.

FIGS. 3–6 illustrate a method of using the device of FIG. 1. FIG. 3 illustrates the baseplate 46 sutured the skin 62 at a tissue site 64. The distal end 14 of the device is adjacent a puncture in a vessel 66 within the tissue site 64. The pigtail 22 is positioned within the utility lumen 16 such that the pigtail extends through the distal end 14 of the device into the vessel 66. A catheter 68 is threaded through the utility lumen 16 and the pigtail into the vessel 66. The catheter can be used to perform a desired medical procedure.

Figure 4:
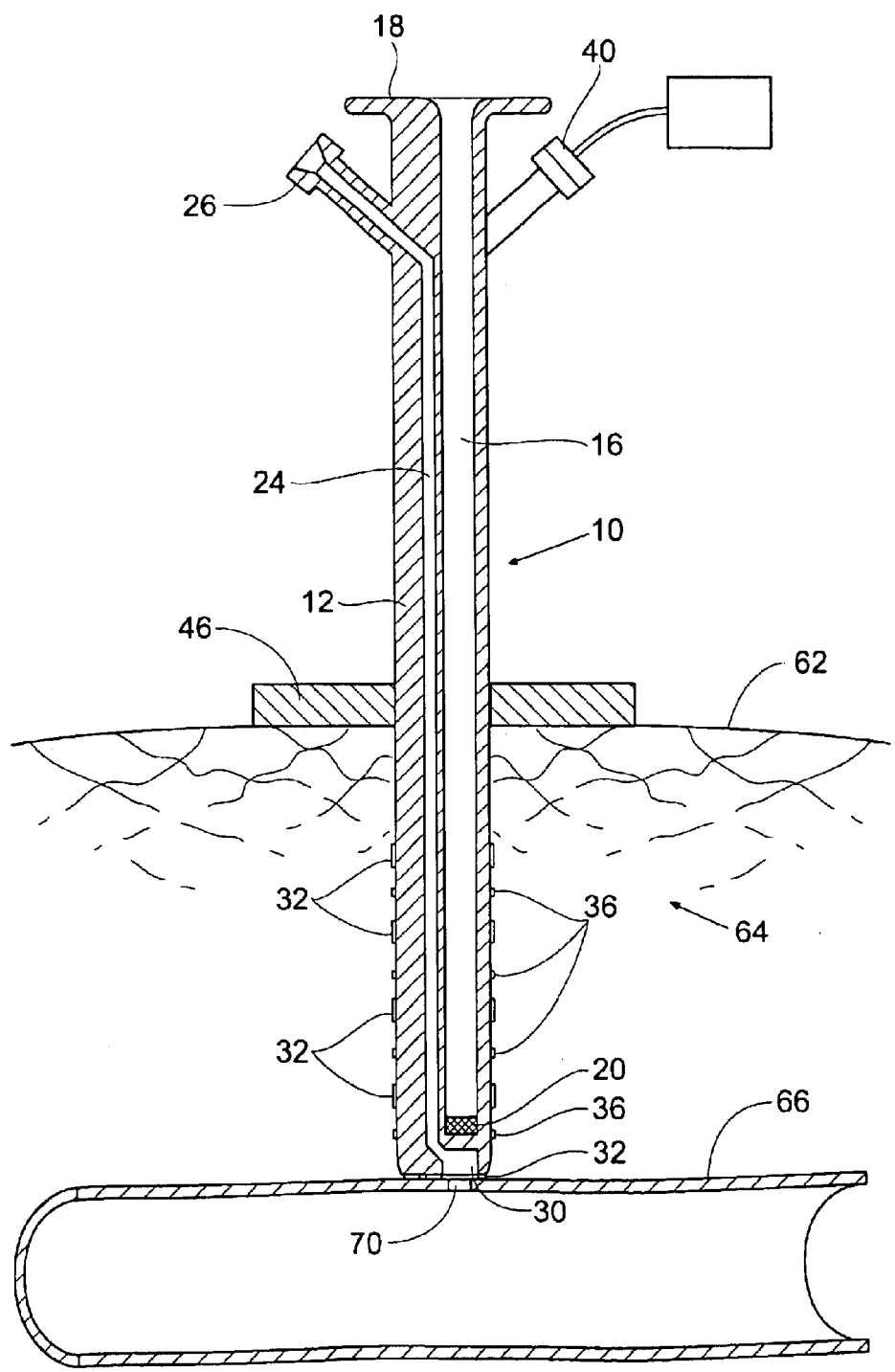
FIG. 4 is a cross section of the closure device of FIG. 3 after the catheter has been removed from the utility lumen.

FIG. 4 illustrates the device after the catheter 68 and pigtail have been removed from the device. As illustrated, removing the catheter and pigtail leaves a puncture 70 in the vessel 66. Blood 72 from the puncture pushes against the distal end 14 of the device. The backflow valve 20 reduces the flow of blood from the vessel 66 into the utility lumen 16.

Figure 5:
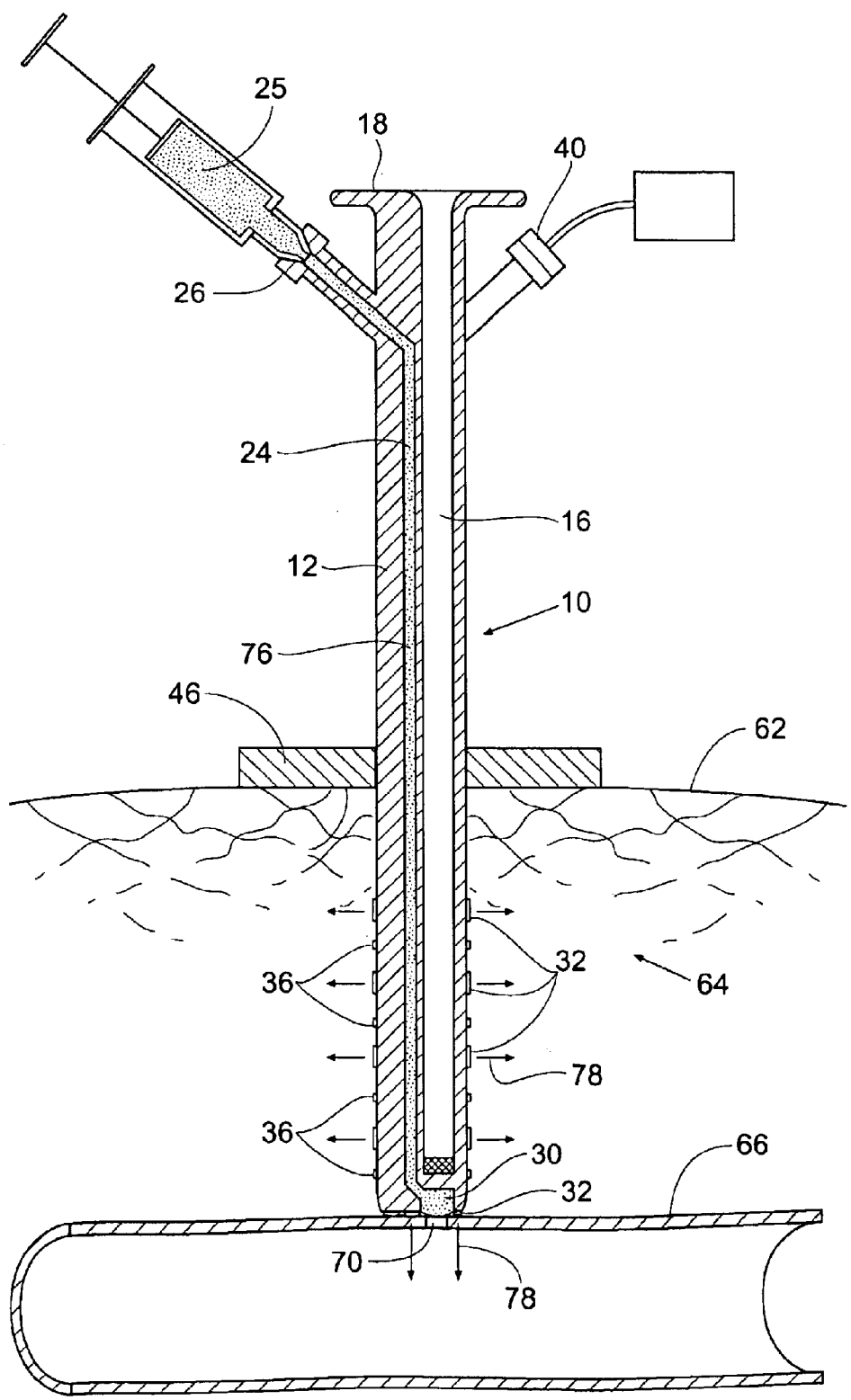
FIG. 5 illustrates the closure of the hole in the vessel achieved by delivering a closure composition adjacent the distal end in combination with the delivery of energy.

In FIG. 5 a closure composition source 25 is coupled with the closure composition port 26. The closure composition 76 is delivered through the closure lumen 24 to the reservoir adjacent the puncture 70. Energy can also be delivered as illustrated by arrows 78. Any form of energy which serves to raise the temperature adjacent the distal end 14 may be used. Examples of types of energy that may be used include RF, microwave, ultrasound, resistive heating, exothermic chemical heating, electromagnetic radiation, actinic radiation, laser, diffused laser, optical energy and frictional heating. The energy used is preferably RF energy.

Figure 6:
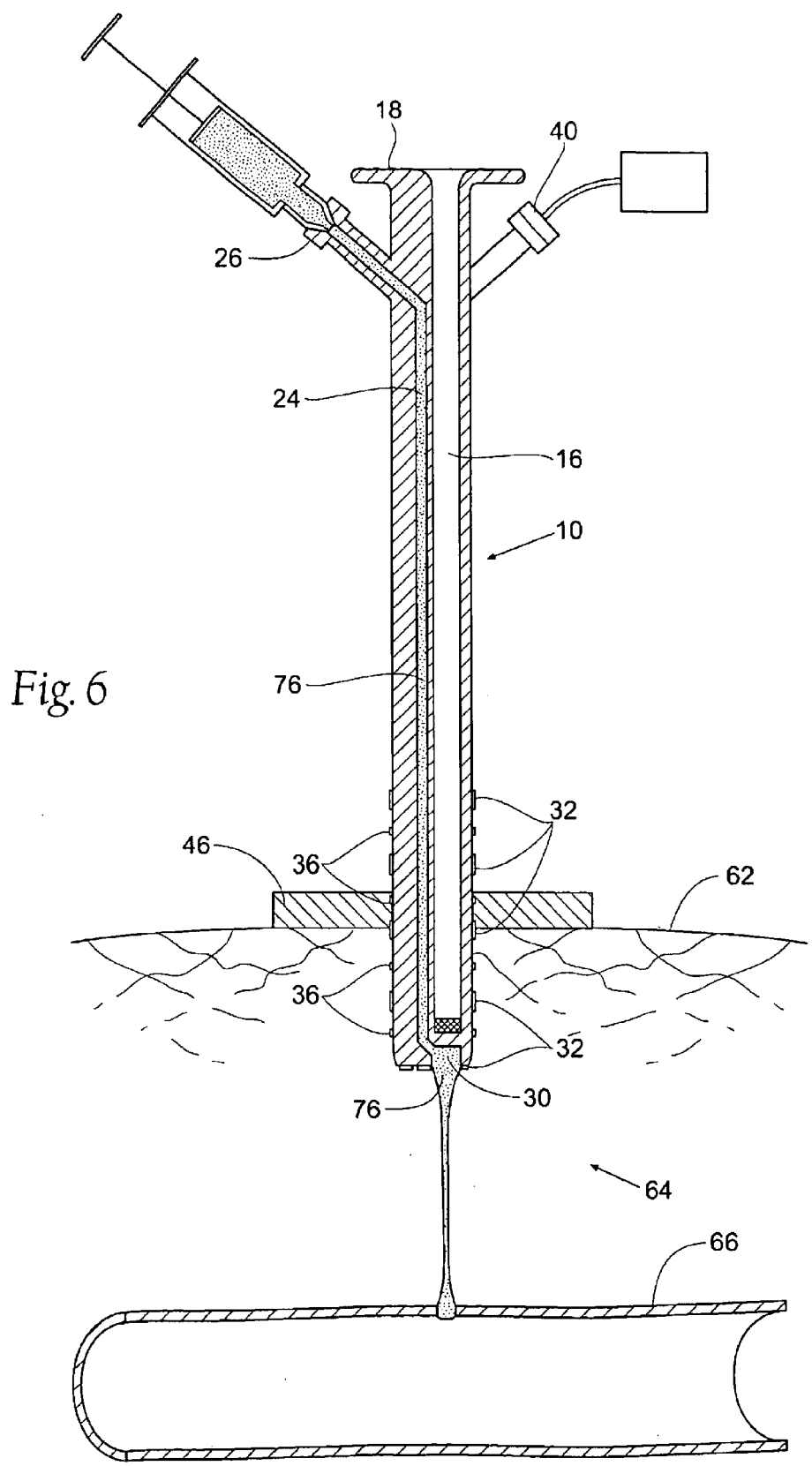
FIG. 6 illustrates the closure device and the vessel after the partial removal of the closure device from the tissue site.

FIG. 6 illustrates the device and the vessel 66 after the partial removal of the device from the tissue site 64. The closure composition is delivered as the device is withdrawn to spread the closure composition along the length of the tissue site 64. As a result, closure of the tissues adjacent the puncture is also effected.

Figure 7A:
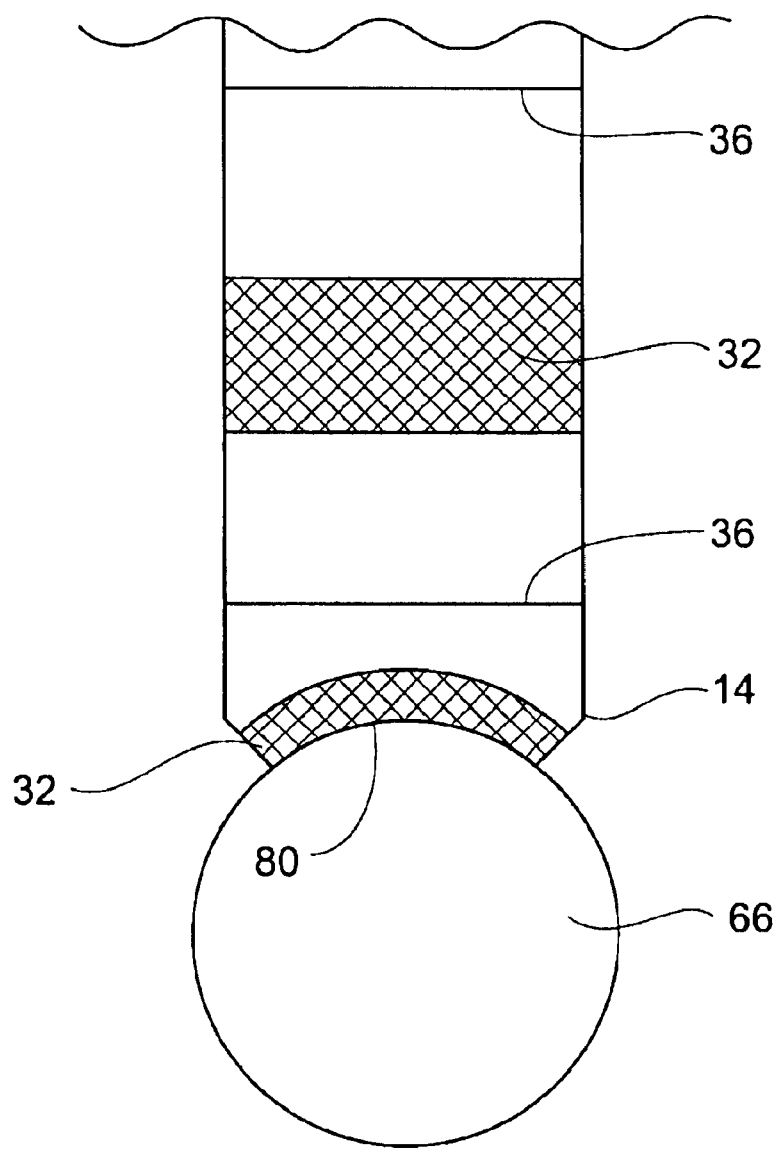
FIG. 7A is a sideview of a closure device with a saddle shaped distal end.

FIG. 7A illustrates a preferred embodiment of the distal end 14 of the device. As illustrated, the distal end 14 is saddle shaped 80 and surrounds a portion of the vessel 66 circumference. Surrounding a portion of the vessel increases the area of contact between the vessel and the distal end of the device. This increased contact area enhances the stability of the distal end 14 relative to the vessel 66. As a result, the opportunity for the distal end 14 to move between withdrawal of the catheter from the vessel and delivery of the closure composition is reduced.

Figure 7B:
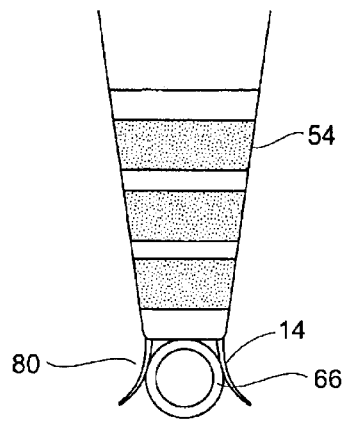
FIG. 7B is a sideview of a closure device with a saddle shaped distal end.
Figure 7C:
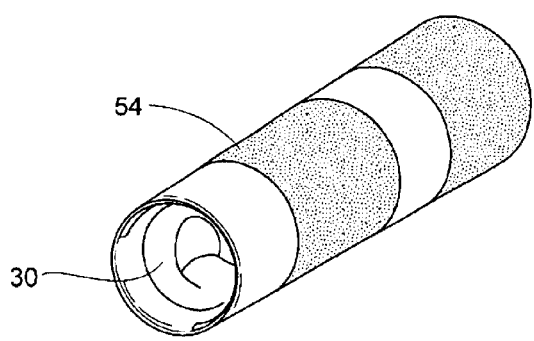
FIG. 7C is a perspective view of the closure device shown in FIG. 7B, illustrating the distal tip in a retracted position.
Figure 7D:
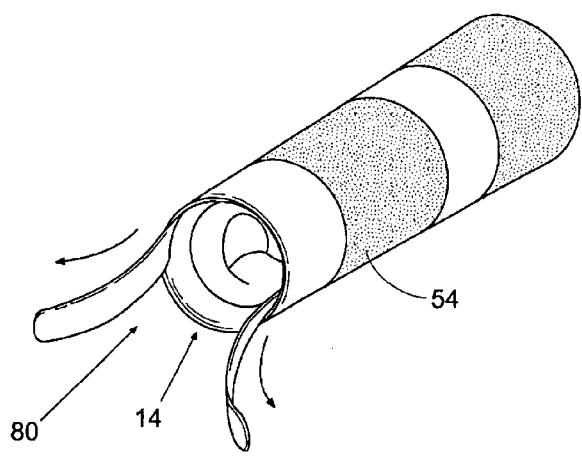
FIG. 7D is a perspective view of the closure device shown in FIG. 7B, illustrating the distal tip in a deployed position.

FIGS. 7B–7D illustrate an alternative embodiment of the saddle shaped 80 distal end 14. The distal end 14 grips a portion of the vessel to enhance the stability of the distal end relative to the vessel.

Figure 8A:
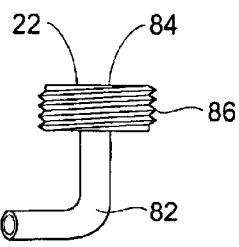
FIG. 8A is a sideview of a pigtail according to the present invention.
Figure 8B:
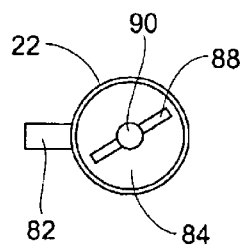
FIG. 8B is a topview of a pigtail according to the present invention.

FIGS. 8A and 8B illustrate an embodiment of a pigtail 22. The pigtail 22 includes a tail portion 82 which is designed to rotate independently of a head portion 84. The head portion 84 includes threads 86, a slot 88 and a hole 90. The tail portion 82 can be manufactured from any flexible and biocompatible tubing, including, but not limited to, TEFLON tubing. The hole in the head portion 84 is aligned with the tubing in the tail portion 82 so a catheter can pass longitudinally through the pigtail 22. The tail portion should be bent when the tail portion 82 is in a relaxed state.

Figure 9A:
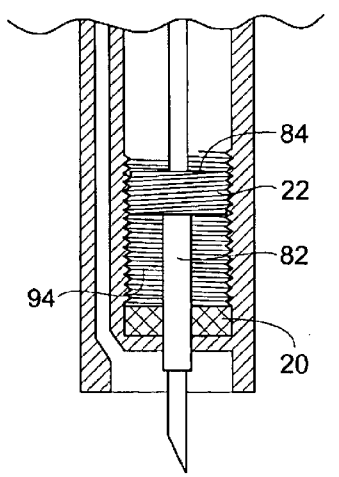
FIG. 9A illustrates a cross section of a closure device including a utility lumen with threads on an inside of the utility lumen. A pigtail within the utility lumen includes a head resting on the threads.
Figure 9B:
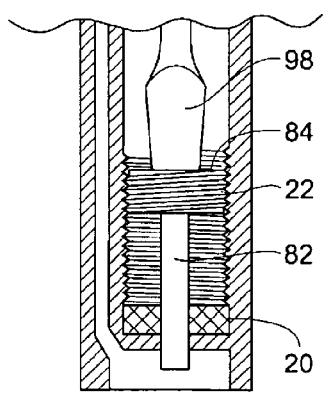
FIG. 9B illustrates a cross section of a closure device with a screwdriver engaging the head section of a pigtail.
Figure 9C:
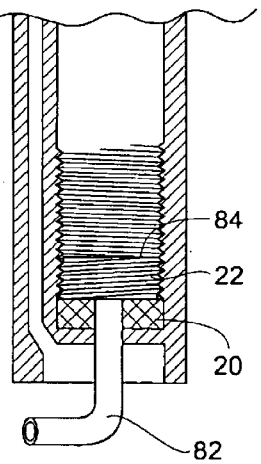
FIG. 9C is a cross section of a pigtail installed within a closure device.

FIGS. 9A–9C illustrate a method of deploying the pigtail 22 within the device. To install the pigtail within the device an instrument 92 is passed through the hole 90 and tail portion 82 of the pigtail 22. The instrument 92 is inserted into the utility lumen 16 and through the distal end 14 of the device. The instrument is then pushed forward until the pigtail rests on a set of threads 94 in the device as illustrated in FIG. 9A. The device threads 94 are sufficiently short that the tail portion 82 of the pigtail is trapped in the backflow valve 20. The instrument 92 can be withdrawn from the pigtail 22. The installation of the pigtail 22 in the device can occur before or after the device has been positioned within a tissue site 64.

In FIG. 9B, the instrument is withdrawn and a screwdriver 98 is inserted into the slot 88 of the pigtail 22. The device threads 94 are complementary to the threads on the head portion 84 of the pigtail 22. Turning the screwdriver 98 can advance or withdraw the pigtail within the utility lumen 16. In FIG. 9C, the pigtail 22 has been advanced until it is adjacent the backflow valve 20 and the screwdriver 98 has been withdrawn. The tail portion returns to its relaxed state after exiting the backflow valve 20.

Figure 10:
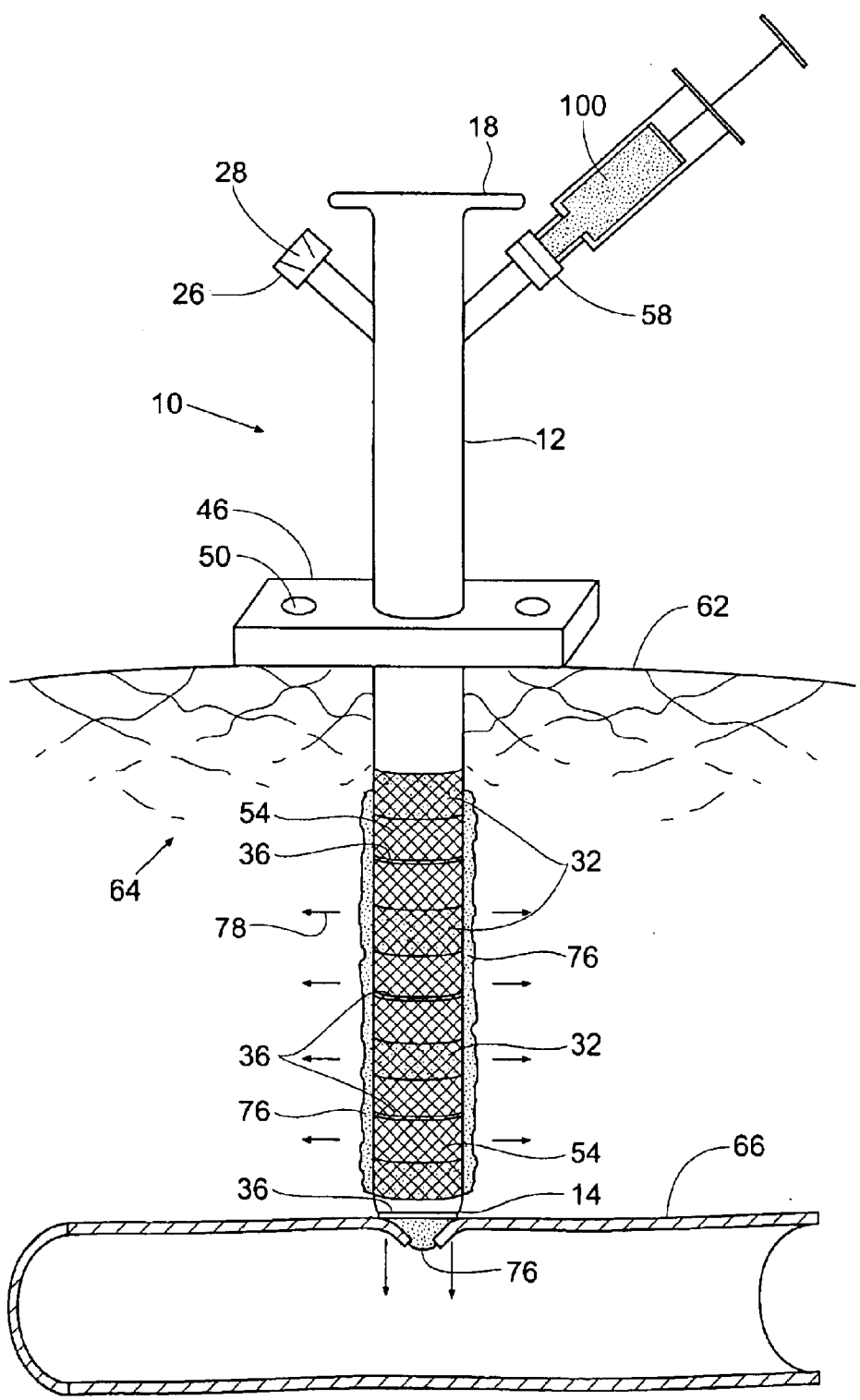
FIG. 10 is a sideview of a closure device with energy and closure composition delivered to tissue adjacent the sides of the closure device as the closure device is retracted from the tissue.
Figure 11:
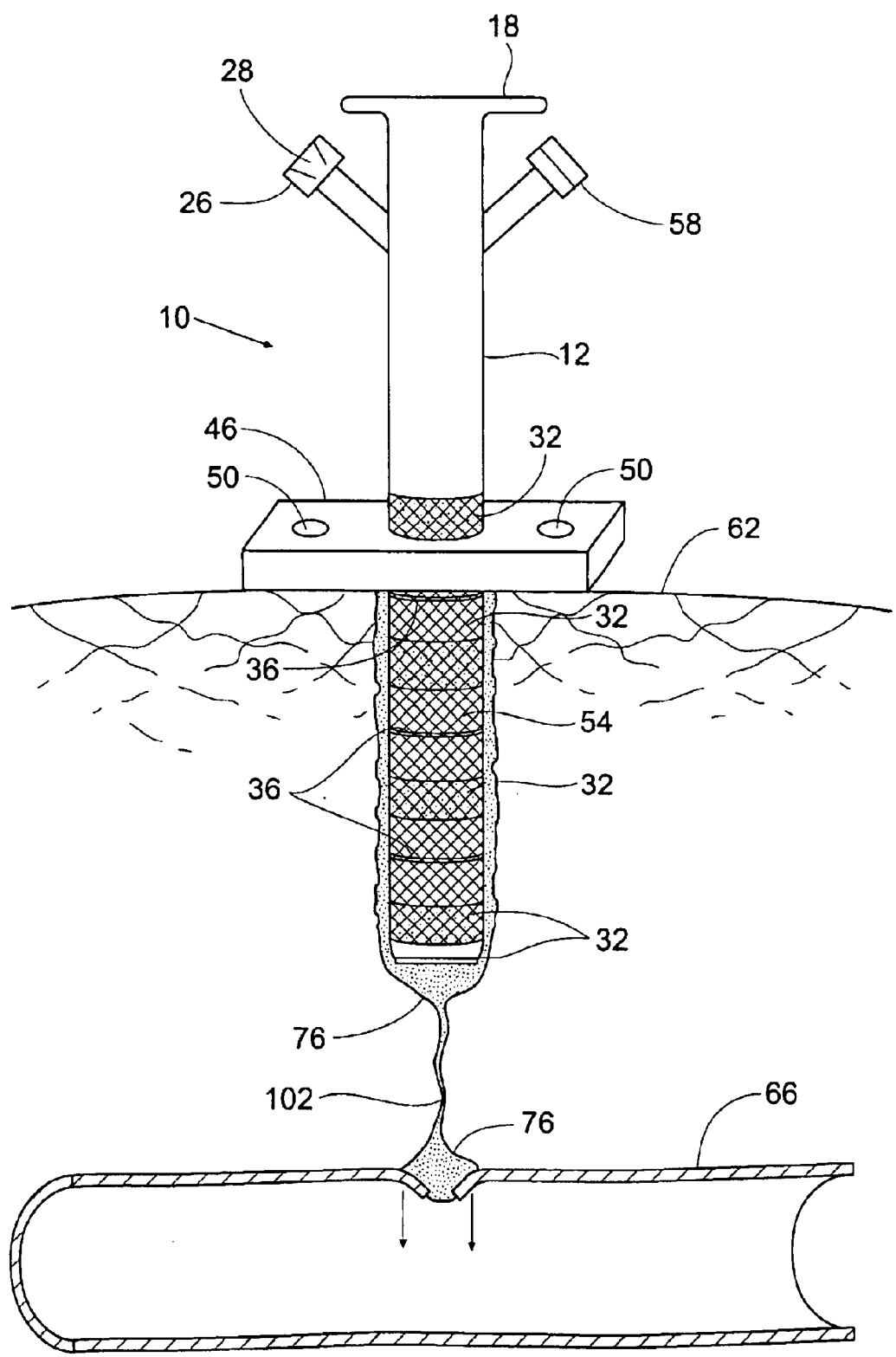
FIG. 11 is a sideview of a tissue site after partial retraction of the closure device.

FIGS. 10–11 illustrate the closure of tissue as the device is withdrawn from the tissue site 64. In FIG. 10, a first closure composition has been delivered to the reservoir and is accumulated against the puncture. A second closure composition source 100 is coupled with the second closure composition port 58. The second closure composition is delivered through the second closure lumen 56 to the microporous membrane 54. The second closure composition passes through the microporous membrane to the tissue adjacent the lateral sides 12 of the device. Energy, indicated by the arrows 78 may also be delivered to the tissue site. In a preferred embodiment, energy and the closure composition are delivered in separate steps, optionally with the delivery of ultrasonic energy either before during or after the delivery of energy and/or the closure composition.

The closure composition within the second closure composition source can be the same as or different from the first closure composition. For instance, the first closure composition may be directed toward closure of the vessel while the second closure composition may be directed at closure of the tissue adjacent the puncture.

The device may be retracted from the tissue site in a continuous motion or in a stepwise fashion. Energy can be delivered to the tissue site before, after or simultaneously with delivery of closure composition. For example, a closure cycle may be used which involves (1) delivering the closure composition; (2) delivering energy; and (3) partially retracting the device. Other sequences for performing these three steps, including performing one or more of these steps at the same time is envisioned and is intended to fall within the scope of the present invention. It is further noted that ultrasonic energy may be delivered simultaneously with any of these steps or in between any of these steps. FIG. 11 illustrates a tissue site after the device has been partially retracted. The closure composition delivered during the retraction causes a tissue union 102.

Figure 12A:
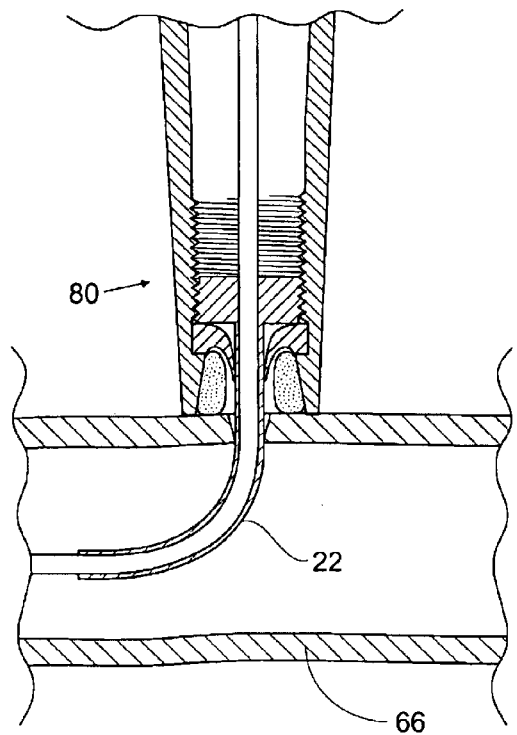
FIG. 12A is a cross section of a closure device with a solid or semi-solid closure composition present at the distal end of the closure device to facilitate the closure of the vessel.
Figure 12B:
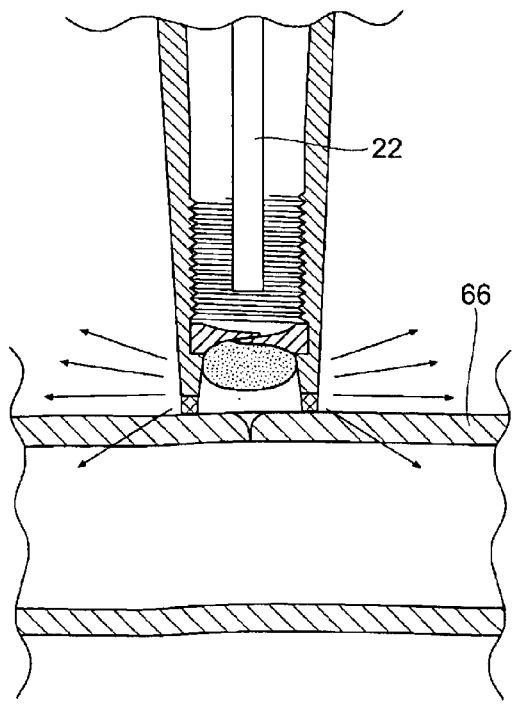
FIG. 12B illustrates the closure device of FIG. 12A with the pigtail retracted.

FIGS. 12A and 12B illustrate an embodiment of the device and a method in which a solid or semi-solid closure composition positioned at the distal end 14 of the device can be used to facilitate closure of the vessel 66. In FIG. 12A the closure composition is positioned within the reservoir 30 and is pushed aside when the pigtail 22 is delivered through the device. When the pigtail 22 is retracted, as illustrated in FIG. 12B, the closure composition is in position to be treated with energy to effect the closure of the vessel 66.

Although the solid or semisolid closure composition is illustrated as being present at the device distal end 14, it should be noted that the solid or semi-solid closure composition may be used in combination with a fluid closure composition delivered through the device distal end 14. Optionally, the solid or semisolid closure composition may be used independently of a fluid closure composition.

A variety of sensors may be used in combination with the devices of the present invention. For example, temperature sensors may be used to detect the temperature adjacent the distal end 14 of the device. A temperature sensor may also be use to detect the temperature adjacent the sides of the device. These temperature sensors are useful for regulating the amount of energy being delivered to the vessel 66 and tissue adjacent the device. Suitable temperature sensors include, but are not limited to, thermocouples. The temperature sensors can have several configurations including, but not limited to, rings which fit around the body of the device or point senors distributed on the body of the device.

A pressure sensor may also be incorporated in the device, preferably at the device distal end 14. The pressure sensor may be used, for example, to determine when the vessel 66 has been sealed, as signaled by a reduction in pressure adjacent the device distal end 14.

Impedance sensors may also be employed when RF is used as the energy in order to monitor the amount of energy being delivered to the tissue.

Figure 13:
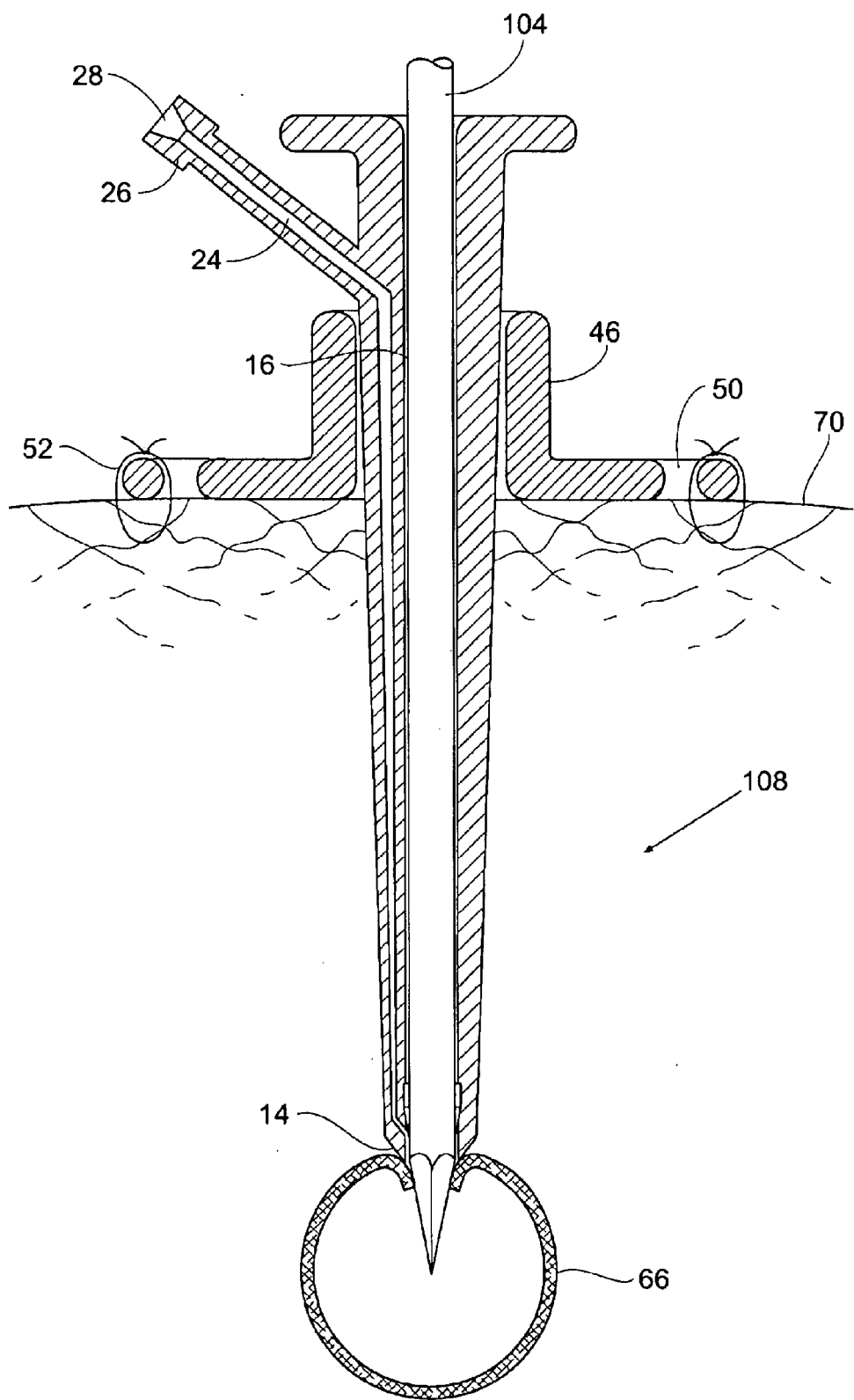
FIG. 13 is a cross section of a closure device with a trocar in place within a utility lumen.

FIGS. 13–17 illustrate a method of using an embodiment of a device and its operation. In FIG. 13, a trocar 104 with a sharpened tip 106 is placed within the utility lumen 16 of the device and is used to puncture the skin 62, muscular tissue 108 and the vessel 66.

Figure 14:
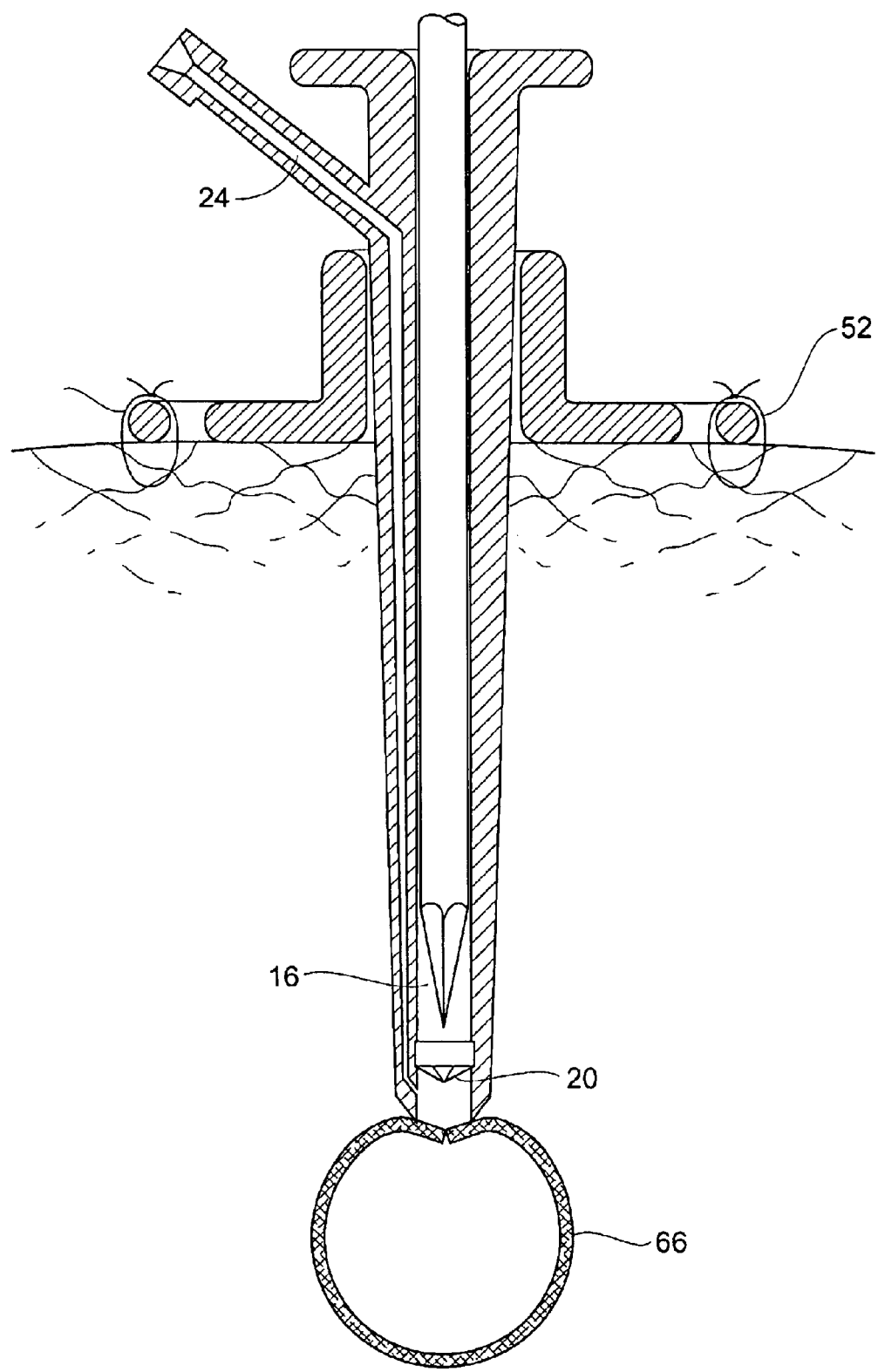
FIG. 14 is a cross section of the closure device of FIG. 13 after the trocar has penetrated the vessel.

In FIG. 14 the trocar 104 is withdrawn and the backflow valve 20 is closed to occlude the utility lumen 16. Closing the utility lumen reduces the loss of blood from the vessel through the utility lumen 16 while exchanging the trocar 104 for another device to be positioned within the utility lumen. The flaps 110 generated in the artery by the penetration of the trocar may partially close, but the degree of closure or whether the flaps of the artery close at all is not important to the function of this invention.

Figure 15:
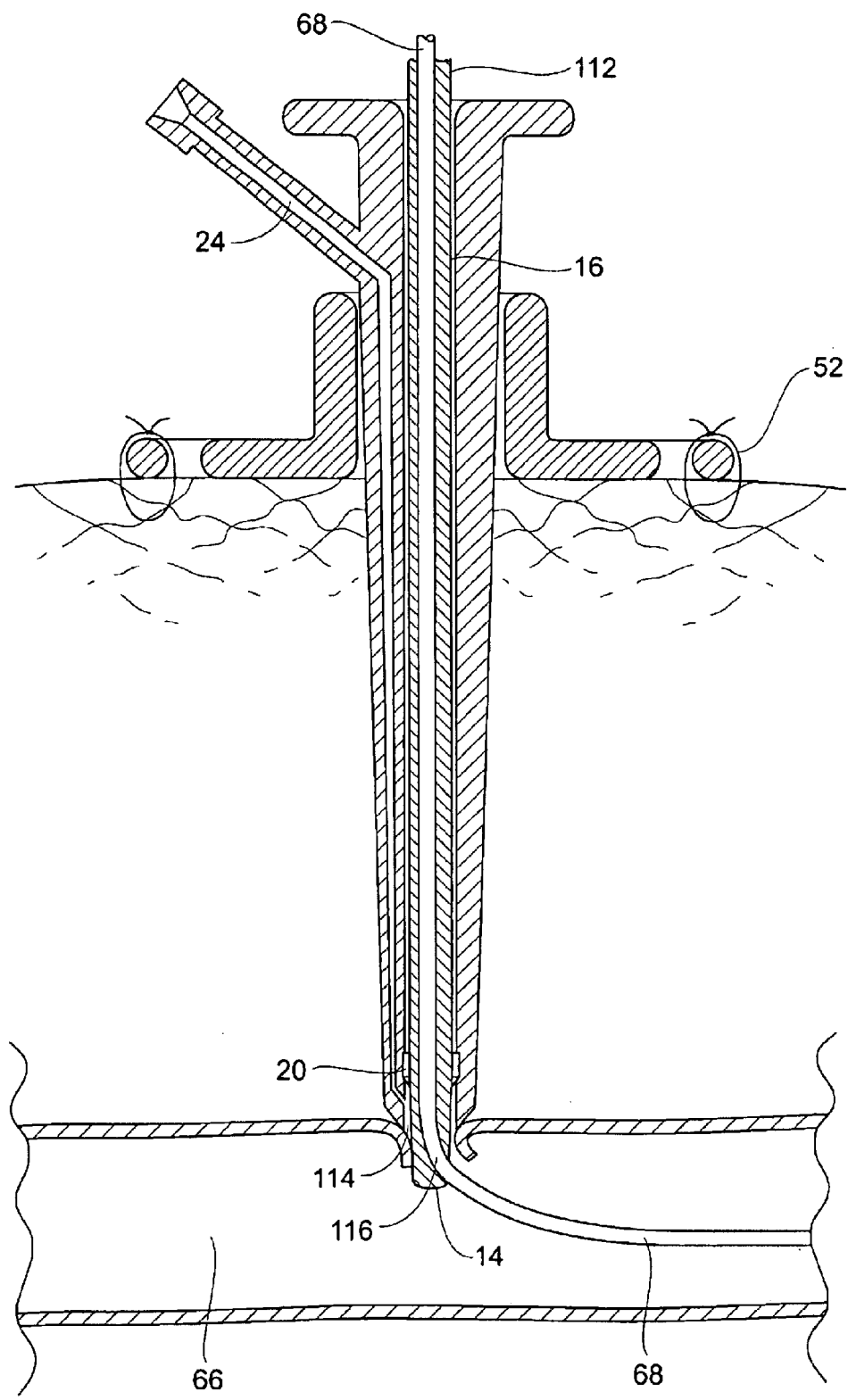
FIG. 15 is a cross section of a closure device with a catheter guide obturator in place within a utility lumen.

Referring to FIG. 15, a catheter guide obturator 112 is placed within the utility lumen 16 of the device and moved forward through the backflow valve 20 to enter the vessel 66. The amount of forward movement of the device may be set (not shown) to a predetermined distance beyond the distal end 14 of the device but since the distal end 14 of the catheter guide obturator 112 has a rounded end, no damage to the vessel 66 will occur if the catheter guide obturator 112 should contact the far wall of the vessel 66. The catheter guide obturator 112 has an internal lumen 114 that is curved 116 near the distal end 14 to direct the catheter 68 in the desired direction within the vessel 66. The backflow valve 20 closes the gap between the outside diameter of the catheter guide obturator 112 and the utility lumen 16 of the device, reducing blood loss from the vessel. In this configuration, the procedure requiring the catheter can be performed.

Figure 16:
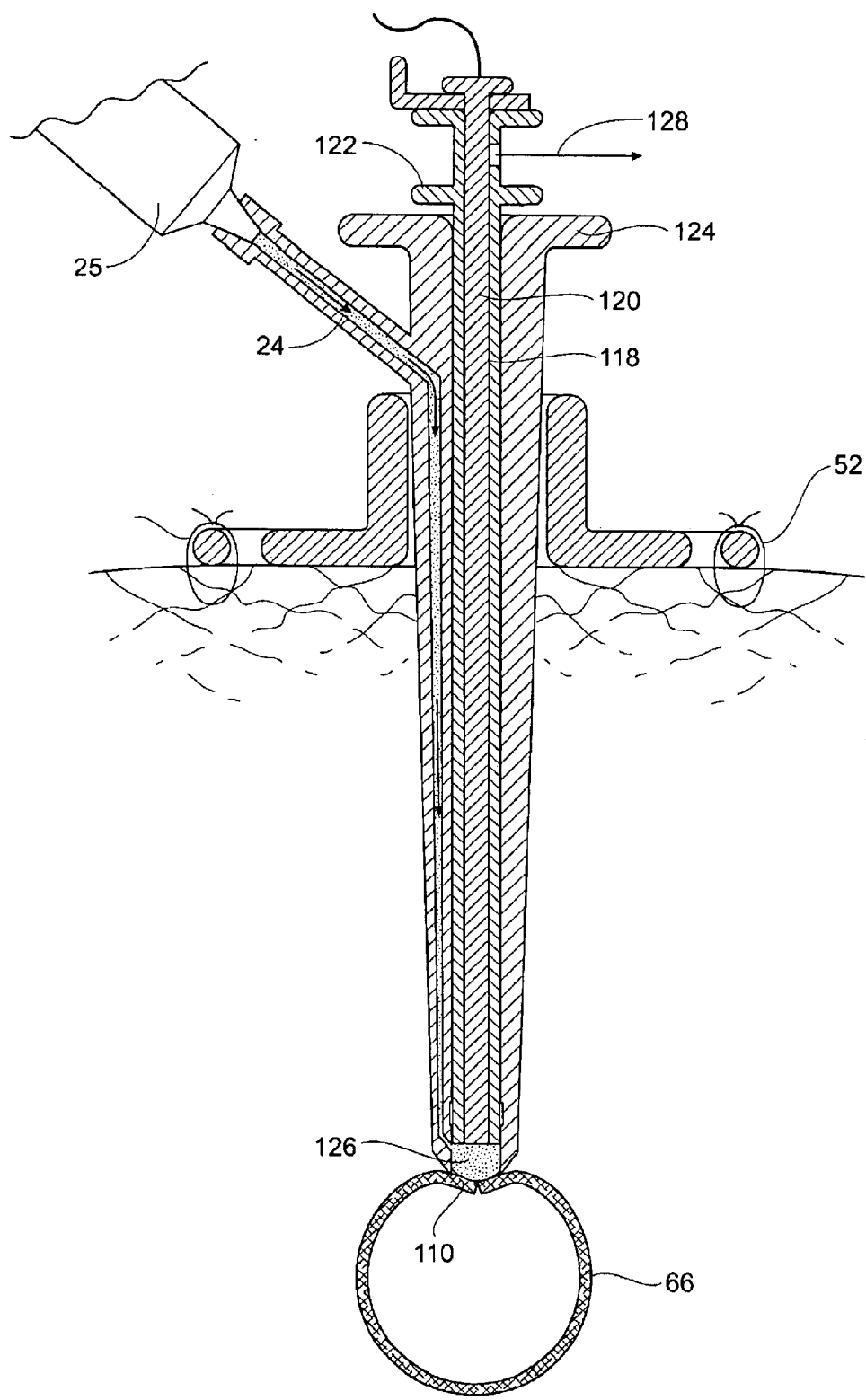
FIG. 16 is a cross section of a closure device with a sealing mold and curing pin in place within a utility lumen.

In FIG. 16, the catheter 68 and catheter guide obturator 112 are withdrawn. A sealing mold 118 with a curing/ejection pin 120 is positioned within the utility lumen 16 of the device. The position of the sealing mold 118 and curing/ejection pin 120 are set with a stop collar 122 as it contacts an upper flange 124 of the device. A shallow cavity 126 is formed at the distal end 14 of the sealing mold 118. This cavity 126 is filled with a closure composition of the present invention which is fed from a closure composition source 25 and passes through the closure lumen 24 to fill the cavity 126. The filling of the cavity 126 can be assisted by suction formed by pulling air through a port 128. This suction may additionally be used to assist in pulling the flaps 110 of the vessel 66 upward against the distal end 14 of the sealing mold 118.

The curing/ejection pin 120 may be constructed from an electrically conductive material. Radio frequency energy passing through the electrically conductive curing/ejection pin 120 to accelerate the polymerization of the closure composition.

FIG. 17 illustrates a distal portion of an embodiment of a device. The device includes a microporous membrane 54 applied to the outer diameter of the device. Side electrodes 32 are positioned at intervals along the length of the body of the device. Alternatively the side electrodes can be a single helix shaped electrode wound around length of the body (not shown). The side electrodes 32 can be positioned over the membrane 54 or beneath the membrane 54 as illustrated. A second closure lumen 56 is incorporated into the device for delivering the closure composition to the outer diameter of the device through the microporous membrane 54. In this regard, the closure composition should have a sufficiently low viscosity to allow the composition to flow through the microporous membrane 54 and against the tissue exposed to the device.

Upon completion of the curing/polymerization of the sealing plug 130, the closure composition will be injected through the second closure lumen 56 and Radio frequency energy will be applied to the annular electrodes 32. The closure composition is preferably of a nature that allows electrical current to flow through the closure composition to enable heating of the composition by the energy being delivered. After a target temperature has been reached, the device is withdrawn. Upon withdrawal, the walls of the tissue site 64 can close in against themselves, the bonding action of the composition will cause adhesion and sealing of the tissue. Additionally, the action of the energy (for example RF energy) on the tissue for the appropriate amount of time and at the proper temperature can promote coagulation. The combination of these factors can provide rapid sealing of the tissue site 64.

A suitable backflow valve 20 is a flapper valve as illustrated in FIG. 18. The flapper valve is preferably formed of an elastomeric material such as medical grade silicone rubber. The configuration, as illustrated by the cross sectional view, may be a cylindrical section transitioning into a conical portion. The conical portion has a series of slits 132 which allow various implements to pass through the valve. The thickness of the flaps 134 and the flexibility of the elastomeric material will be balanced to provide memory sufficient to close the opening as the implements are withdrawn and provide a fluid seal. Blood pressure against the outer surface of the cone will cause the flapper valve to close more tightly.

Figure 19:
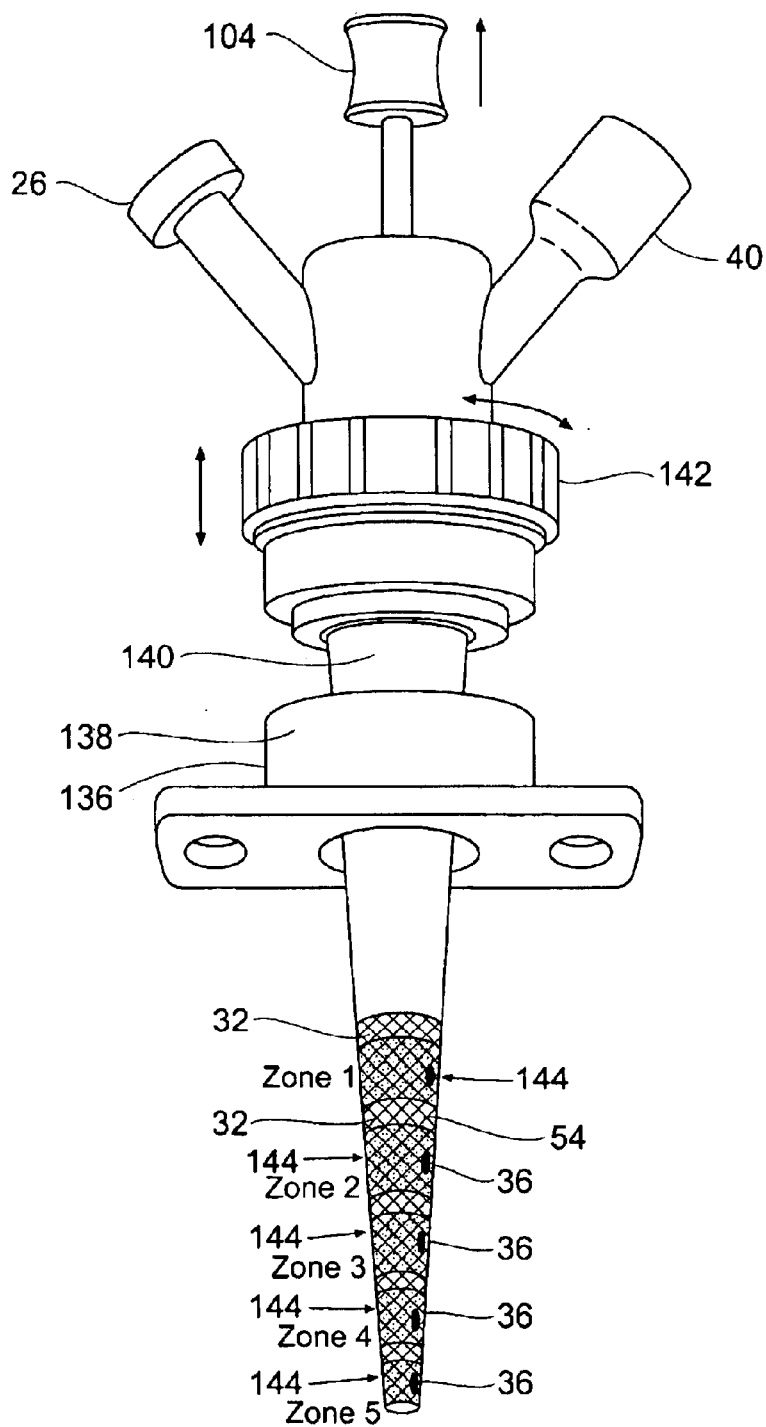
FIG. 19 is a sideview of a closure device including an automatic retraction device.

FIG. 19 illustrates yet another embodiment of the present invention. A removable trocar 104 is temporarily positioned in the utility lumen of the device. The trocar has a pointed tip which can be used for puncturing the skin, tissue and blood vessel to allow the placement of the device into the tissue and into a femoral artery. Closure composition port 26 provides a channel through which the closure composition may be introduced through a closure lumen (not shown) to microporous membrane 54. The closure lumen allows the closure composition to pass through the microporous membrane 54 into the tissue. As illustrated, segments of the microporous membrane 54 are separated by side electrodes 32, the controls attachment port 40 being for RF energy. It should be noted, however, that the device may be adapted for delivery of other forms of energy as described above.

The temperature sensors 36 are used to sense the temperature adjacent the distal end 14. The temperature feedback may be pre-set as well as adjusted during use.

In the embodiment illustrated, temperature sensors are operatively coupled with an automated device withdrawal system 136. The temperature sensors can activate springs 138 within a rack 140 coupled with the main member 142. The activation of the springs causes the device to be withdrawn from the tissue site. As a result, withdrawal of the device can be correlated with the temperatures at various zones 144 within the tissue site. For example, as zone one reaches a specific predetermined temperature, the springs become activated and the rack 140 partially withdraws the device. As each subsequent zone meets a pre-determine temperature, the device is withdrawn further. Suitable predetermined temperatures include, but are not limited to, 45–50° C. This withdrawal sequence can be repeated until the device is withdrawn through zones five, four, three, two, and one. Closure composition can be delivered before after and during the withdrawal of the device. As a result, the device leaves the vessel sealed and the tissue welded together as the device is withdrawn.

FIGS. 20–22 illustrates the use of the device of FIG. 19 where the vessel 66 is a femoral artery. FIG. 20 illustrates a plurality of sutures holding the device in position at a tissue site. FIG. 21 shows the catheter introduced into the femoral artery for performance of a surgical procedure.

FIG. 22 shows the withdrawal of the catheter and the device. During withdrawal of the device, closure composition is delivered to the tissue site 64 through the microporous membrane and RF energy is applied. As the temperature elevates and the closure composition infused, the temperature sensor 36 indicates to the spring system that the device should start to back away. As it backs away, it seals the tissue through elevated temperature, saline, and collagen infusion, achieving a capillary flow and molecular bonding. The whole area is sealed as the device is retracted. The device is then removed, and a plaster is applied to the wound.

Figures 23A, 23B, 23C:
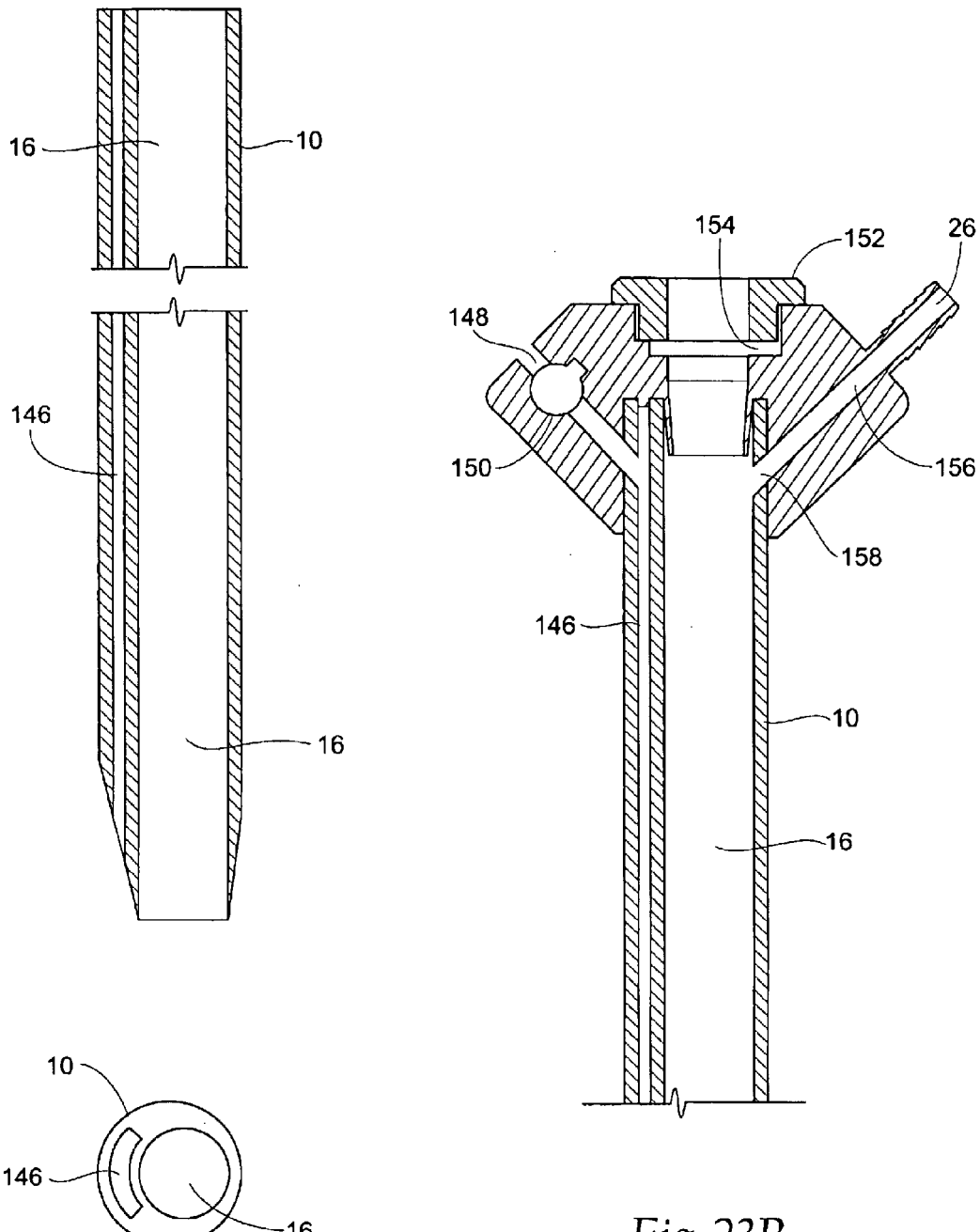
FIG. 23A is a longitudinal cross section of a distal end of a closure device.
FIG. 23B is a cross section of a proximal end of a closure device for use with an obturator.
FIG. 23C is a vertical cross-section of a distal end of a closure device.

FIGS. 23A–23C illustrate another embodiment of the present invention. The body 10 includes a central lumen 16 and a bloodspurt lumen 146. A blood spurt port 148 with a shutoff valve 150 opens into the bloodspurt lumen 146 and a closure composition port 26 opens into the utility lumen 16. At the proximal end of the body is a stop collar 152 configured to accommodate the proximal end of an obturator. A catch cannel 154 is positioned within the proximal end of the body 10. A first closure lumen 156 has a closure composition port 26 through which one or more fluent closure compositions can be delivered into the closure lumen. The first closure lumen includes an exit port 158 through which the one or more fluent closure composition precursors can be delivered from the first closure lumen to the utility lumen 16.

Figures 24A, 24B:
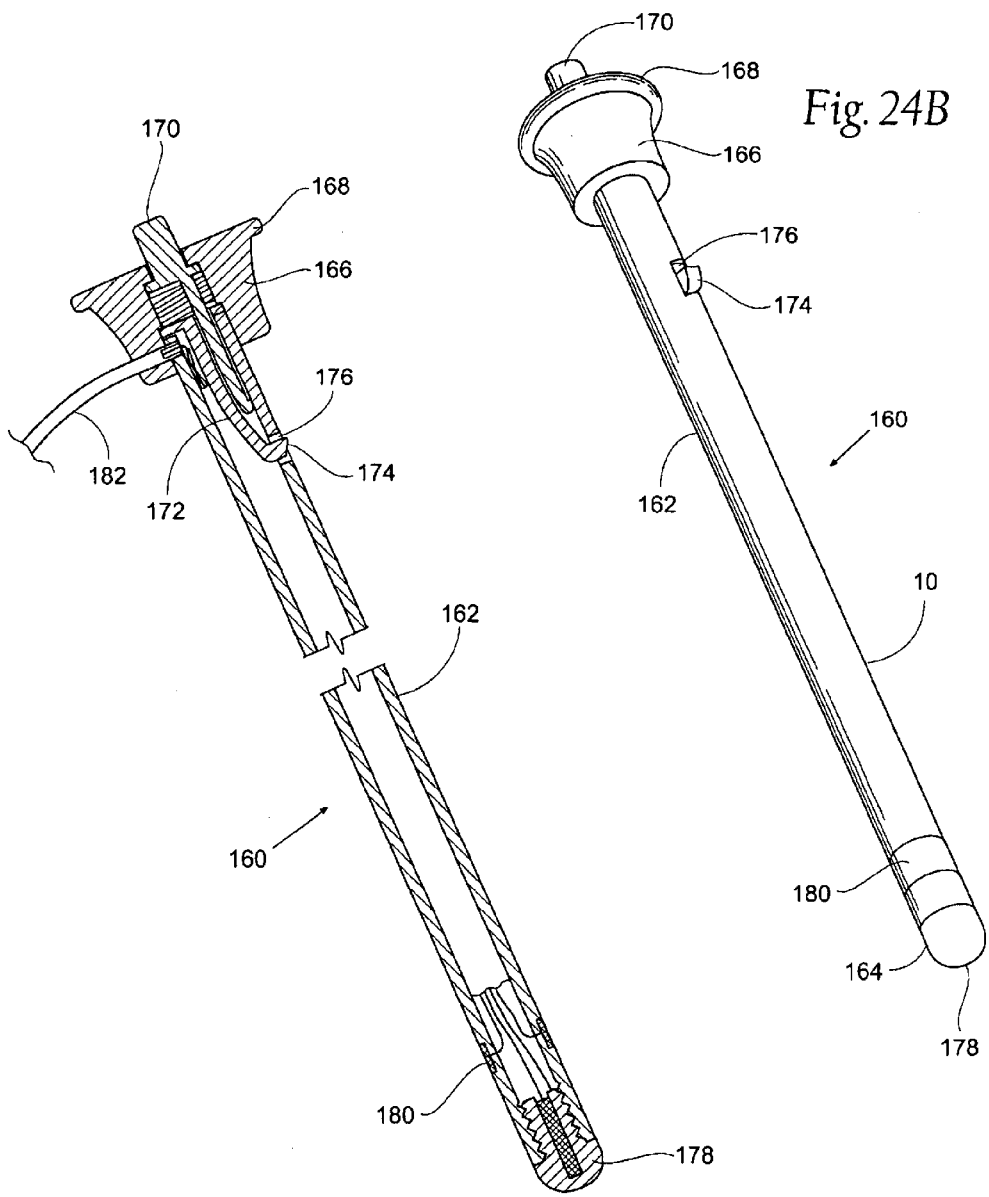
FIG. 24A is a cross section of an obturator for use with the closure device illustrated in FIG. 23A.
FIG. 24B is a side view of an obturator for use with the embodiment illustrated in FIG. 23A.
Figure 25A:
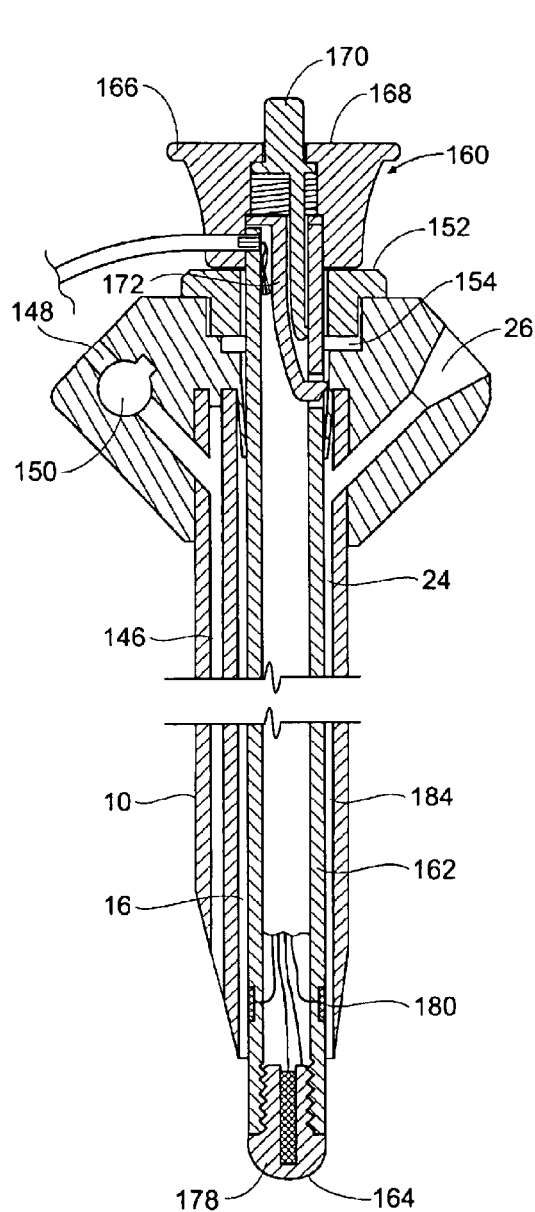
FIG. 25A is a cross section of the obturator of FIG. 24A installed in the utility lumen of the closure device of FIG. 23A.
Figure 25B:
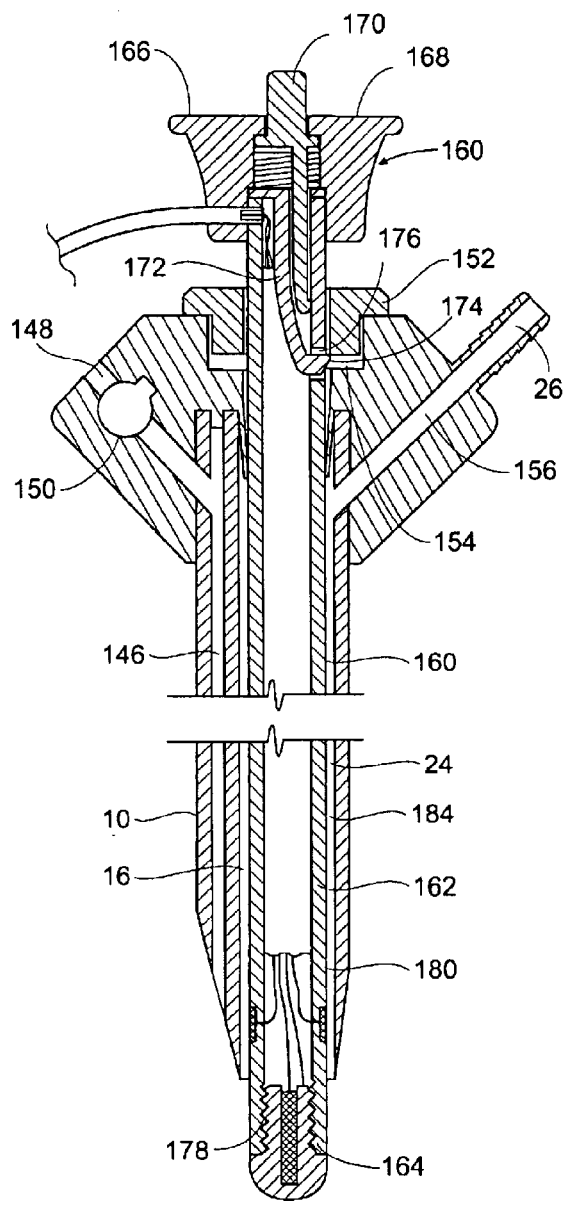
FIG. 25B is a cross section of the obturator of FIG. 24A installed within the closure device of FIG. 23A and withdrawn though the central lumen until a catch on the obturator engages a catch channel on the closure device.

FIGS. 24A and 24B illustrate an obturator 160 for use with the body 10 of FIGS. 25A and 25B. The obturator 160 includes an obturator body 162 with a distal end 164 and a proximal end 166 with an enlarged head 168. A spring biased obturator knob 170 is positioned at the proximal end 166. The obturator knob 170 is coupled to an internal latch 172. The latch includes a catch 174 which extends through an opening 176 in the obturator body 162. Turning the obturator knob 170 causes the catch 174 to withdraw through the obturator body 162. The obturator body 162 further includes a distal electrode 178 and side electrodes 180. A temperature sensor 36 such as a thermocouple 36 is secured within the distal electrode 178 by potting composition. An additional temperature sensor 36 is coupled to the inner surface of the side electrode 180. Radiofrequency conductors and thermocouple wires feed through the internal diameter of the obturator body 162 in a connector cable 182.

FIGS. 25A and 25B illustrate the obturator 160 disposed within the device body 10. In FIG. 25A the enlarged head 168 of the obturator 160 contacts the stop collar 152 and prevents the obturator from sliding further into the device body. The external diameter of the obturator 160 is smaller than the diameter of the utility lumen 16. As a result, the obturator 160 partially defines a second closure lumen 184 between the obturator and the elongated body. The second closure lumen is coupled with the first closure lumen and is configured to receive closure composition delivered through the first closure lumen. The obturator can be withdrawn relative to the device along arrows 186 until the catch 174 engages the catch channel 154 as illustrated in FIG. 27B.

Figure 26:
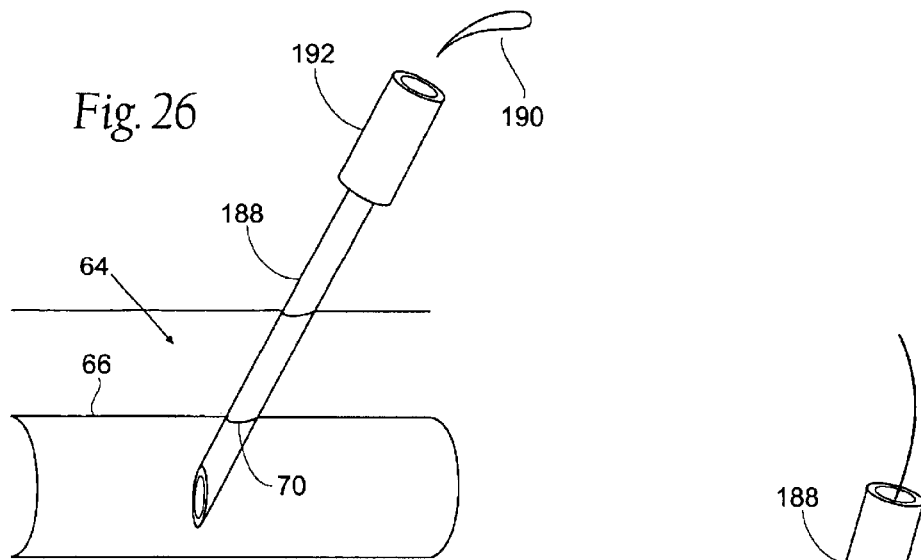
FIG. 26 is a sideview of a hollow needle penetrating a vessel.

FIGS. 26–34 illustrate operation of the device of FIG. 23. As illustrated in FIG. 26, a hollow needle 188 is inserted through the tissue site 64 until the vessel 66 is punctured. Location of the needle 188 within the vessel 66 is confirmed by a blood spurt 190 from the proximal end 192 of the needle 188.

Figure 27A:
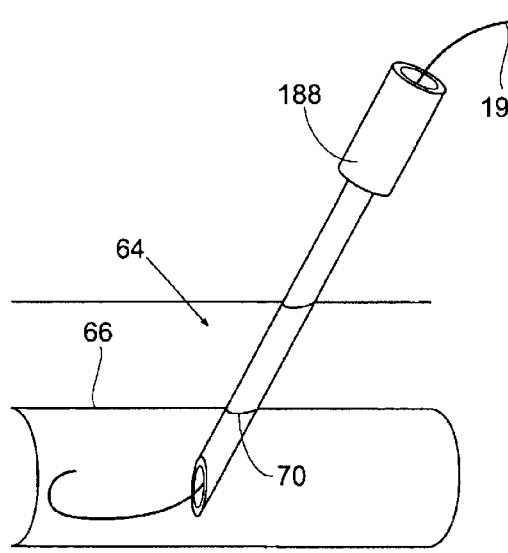
FIG. 27A is sideview of a guidewire threaded through the hollow needle of FIG. 26.
Figure 27B:
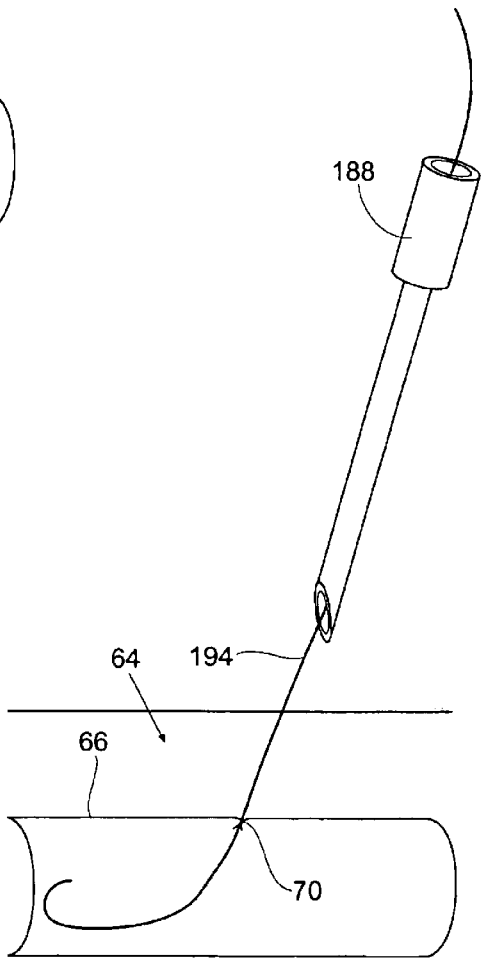
FIG. 27B illustrates the needle withdrawn from the tissue site along the guidewire.
Figure 28:
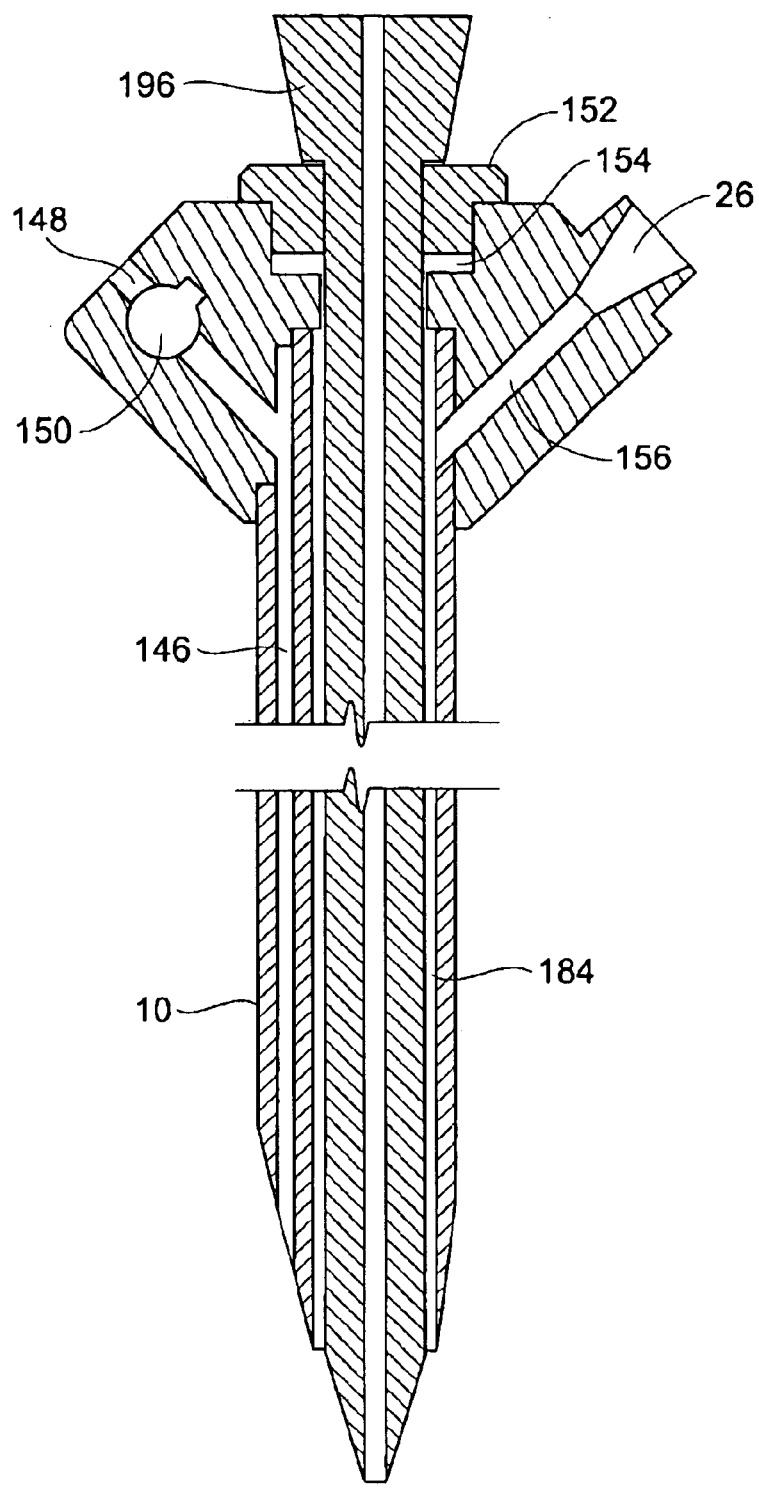
FIG. 28 is a cross section of a closure device. A hollow dilator is installed within the utility lumen of the closure device.

In FIG. 27A a guidewire 194 is fed through the needle 188 into the vessel 66. In FIG. 27B the needle 188 is withdrawn along the guidewire 194 leaving the guidewire 194 in place. In FIG. 28, a hollow dilator 196 is placed in the utility lumen 16 of the device.

Figure 29:
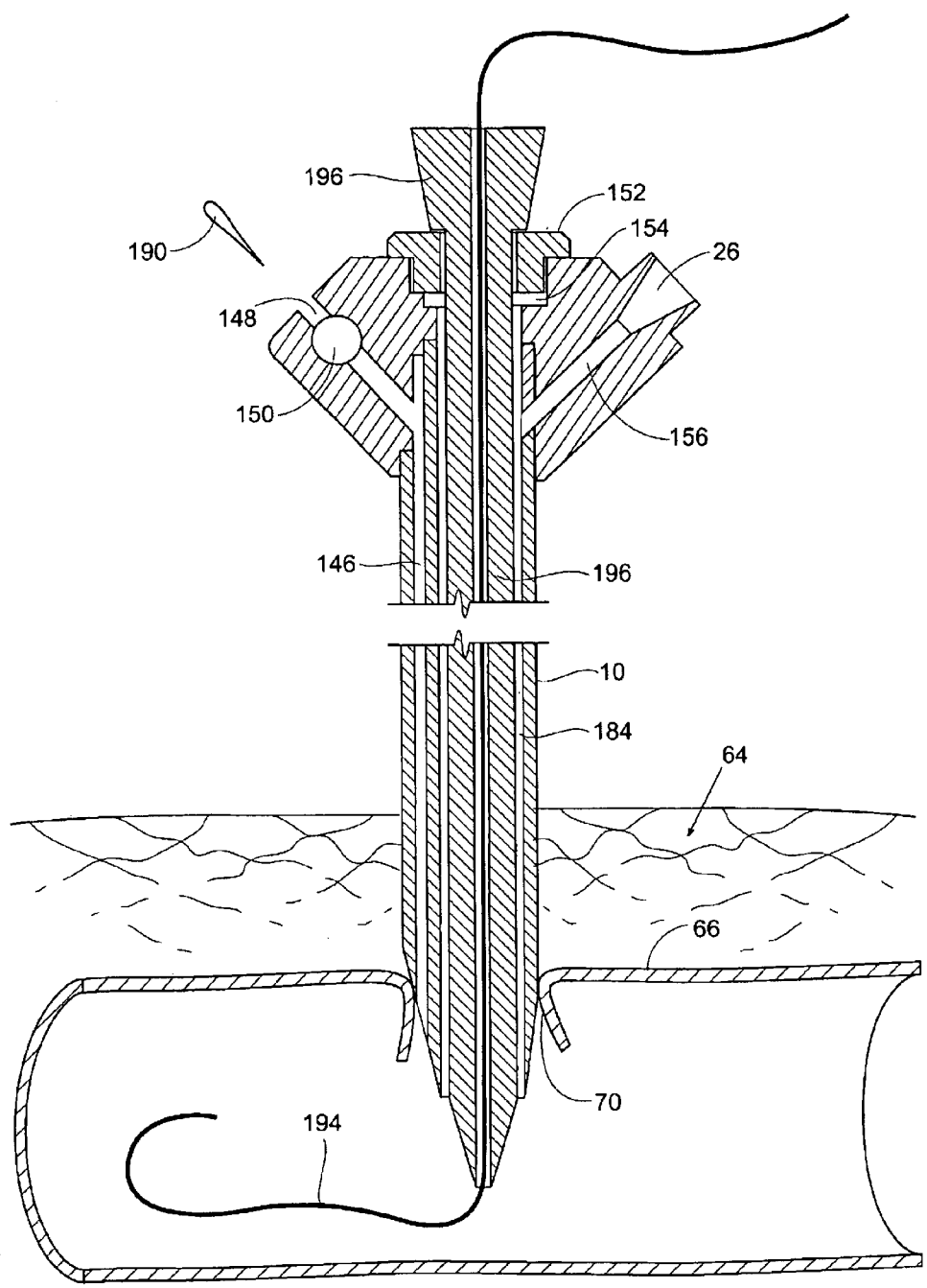
FIG. 29 is a cross section of the dilator and closure device of FIG. 28 threaded over a guidewire and advanced through a tissue site to puncture a vessel.

In FIG. 29, the guidewire 194 is threaded though the dilator 196 which is pushed forward along the guidewire 194 into the tissue site 64 to dilate the puncture 70. The advancement of the device is stopped once the distal end 14 is within the vessel 66 as indicated by a bloodspurt from the bloodspurt lumen 146.

Figure 30:
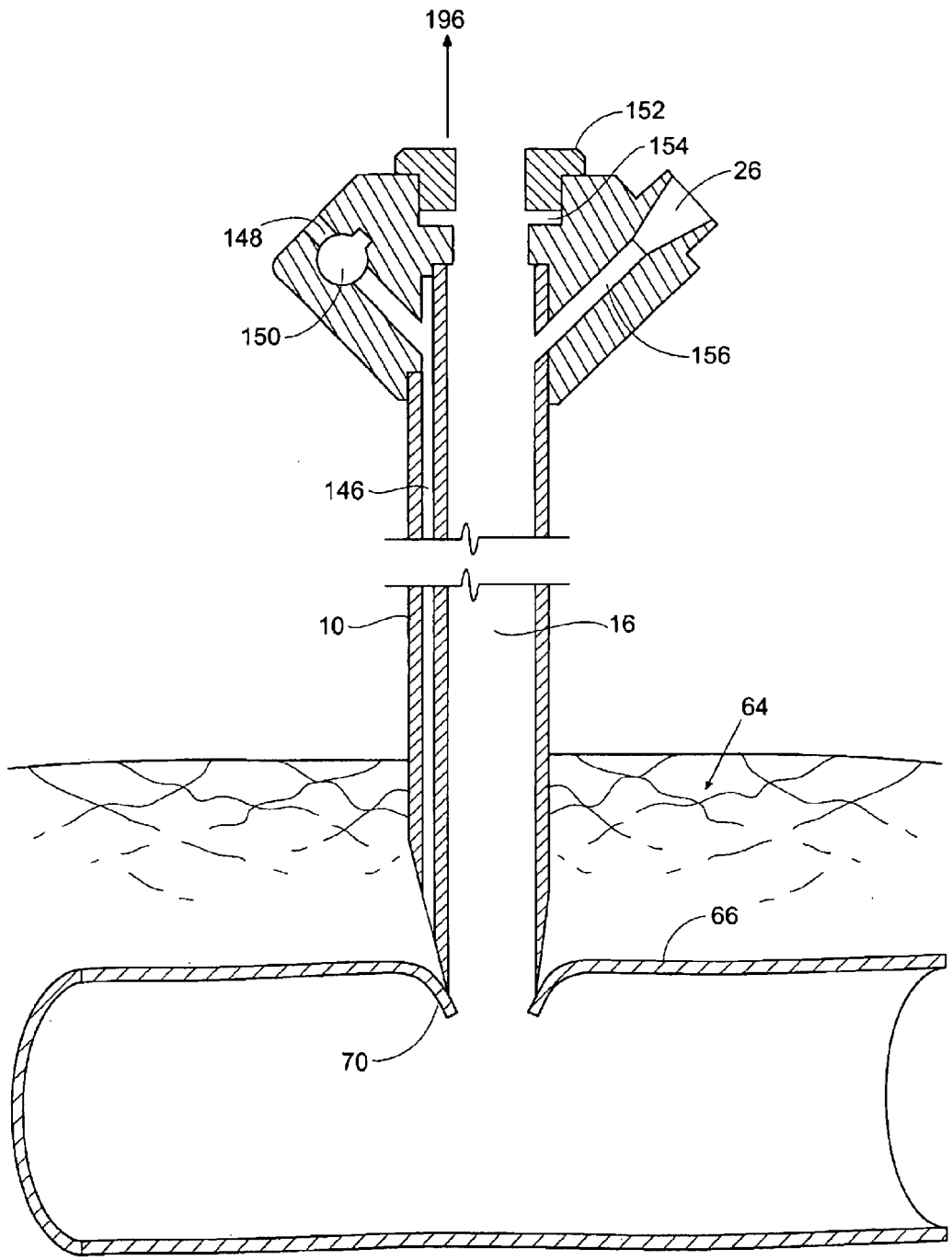
FIG. 30 is a cross section of the closure device of FIG. 29 withdrawn from the puncture so the distal end is adjacent the puncture outside the vessel.

In FIG. 30, the dilator 196 and guidewire 194 are withdrawn from the lumen 16. The device is withdrawn in the direction of the arrow 198 until the distal end 14 is positioned outside the vessel 66 adjacent the puncture 70. The position of the distal end 14 outside the vessel 66 is indicated when the bloodspurt ceases. At this stage, a catheter or other device can be fed through the utility lumen and surgical procedures performed. Upon completion of the procedure, the catheter and sheath are removed from the device. A backflow valve 20 can be included at the distal end 14 to reduce blood loss.

Figure 31:
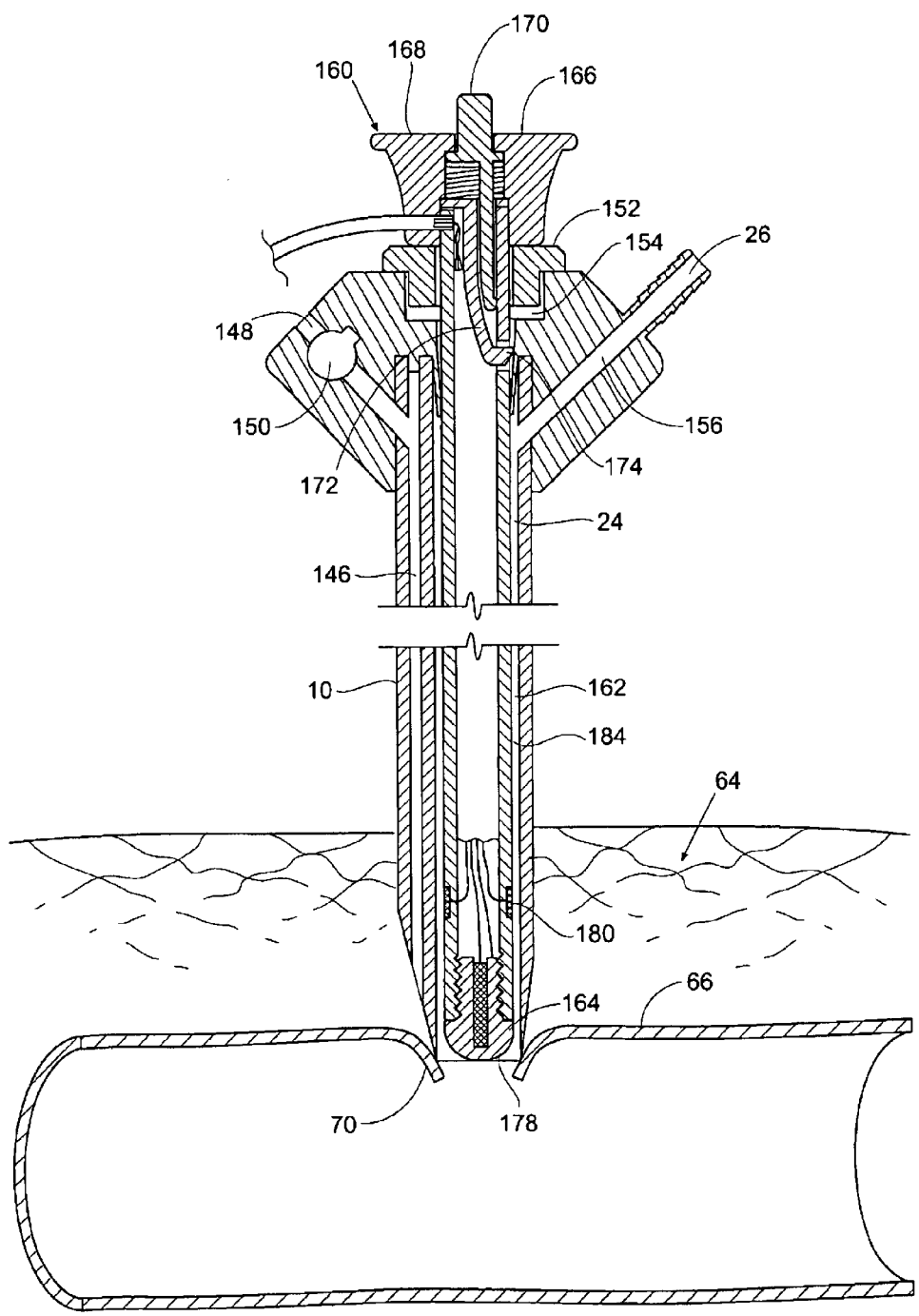
FIG. 31 is a cross section of an obturator installed within the utility lumen of the closure device of FIG. 30.

In FIG. 31, the obturator 160 is placed in the utility lumen 16 until the enlarged head 168 of the obturator 160 contacts the stop collar 152 of the device. The obturator has a length such that when the enlarged head of the obturator 160 contacts the stop collar, the distal end 164 of the obturator 160 extends slightly beyond the distal end 14 of the device or is flush with the distal end 14 of the device as illustrated. Since the distal end 14 of the device is positioned outside the vessel 66 adjacent the puncture 70, the distal end 164 of the obturator is positioned outside the vessel 66 adjacent the puncture 70.

Figure 32:
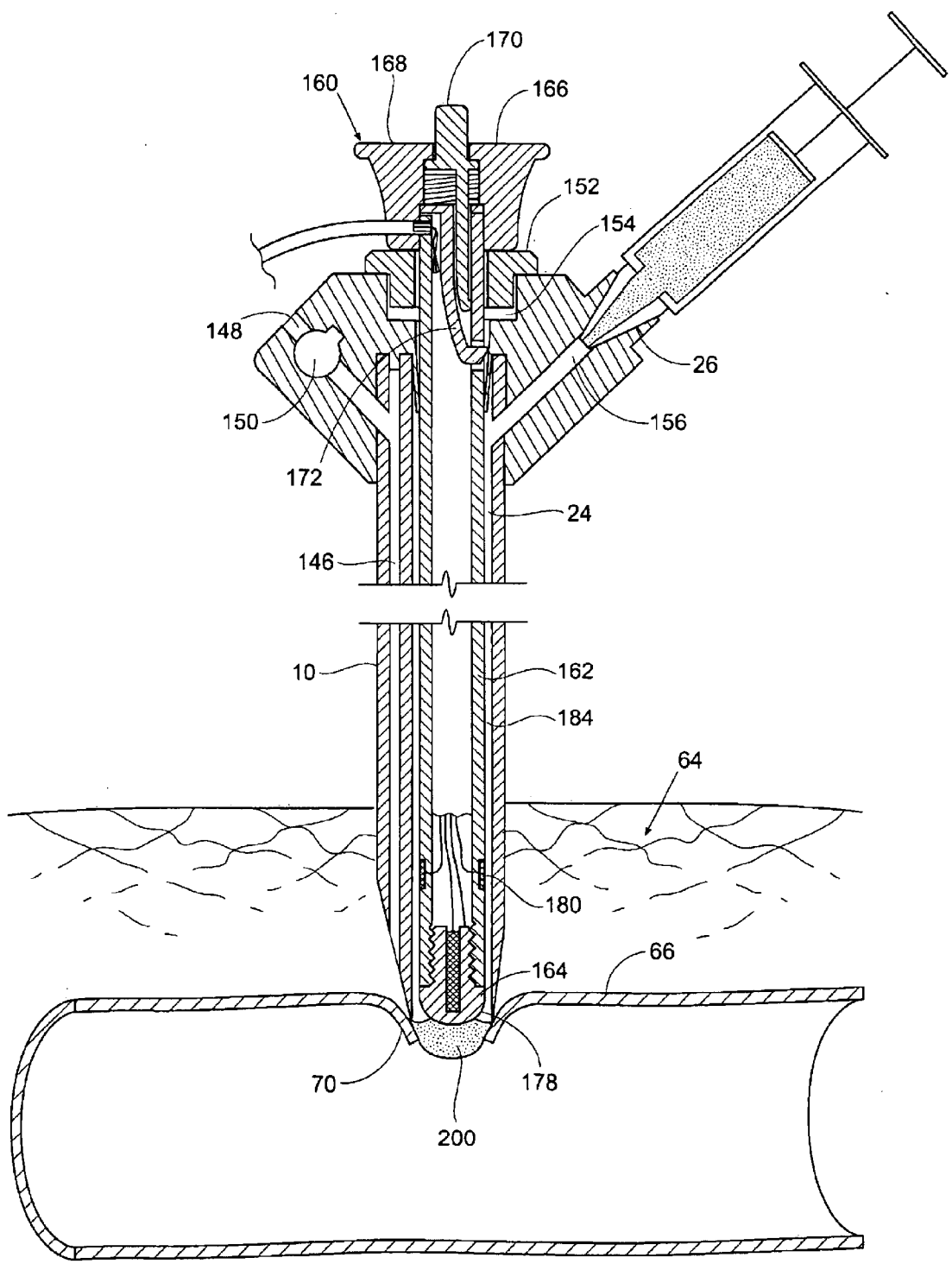
FIG. 32 illustrates a closure composition source coupled with the closure device of FIG. 31.

In FIG. 32 RF energy is applied from the distal electrode 178. The energy coagulates the blood and protein near the puncture 70. Additionally, a closure composition source 25 can be coupled to the closure composition port 26 and closure composition applied. The energy and closure composition create a first seal 200 at the puncture 70.

Figure 33:
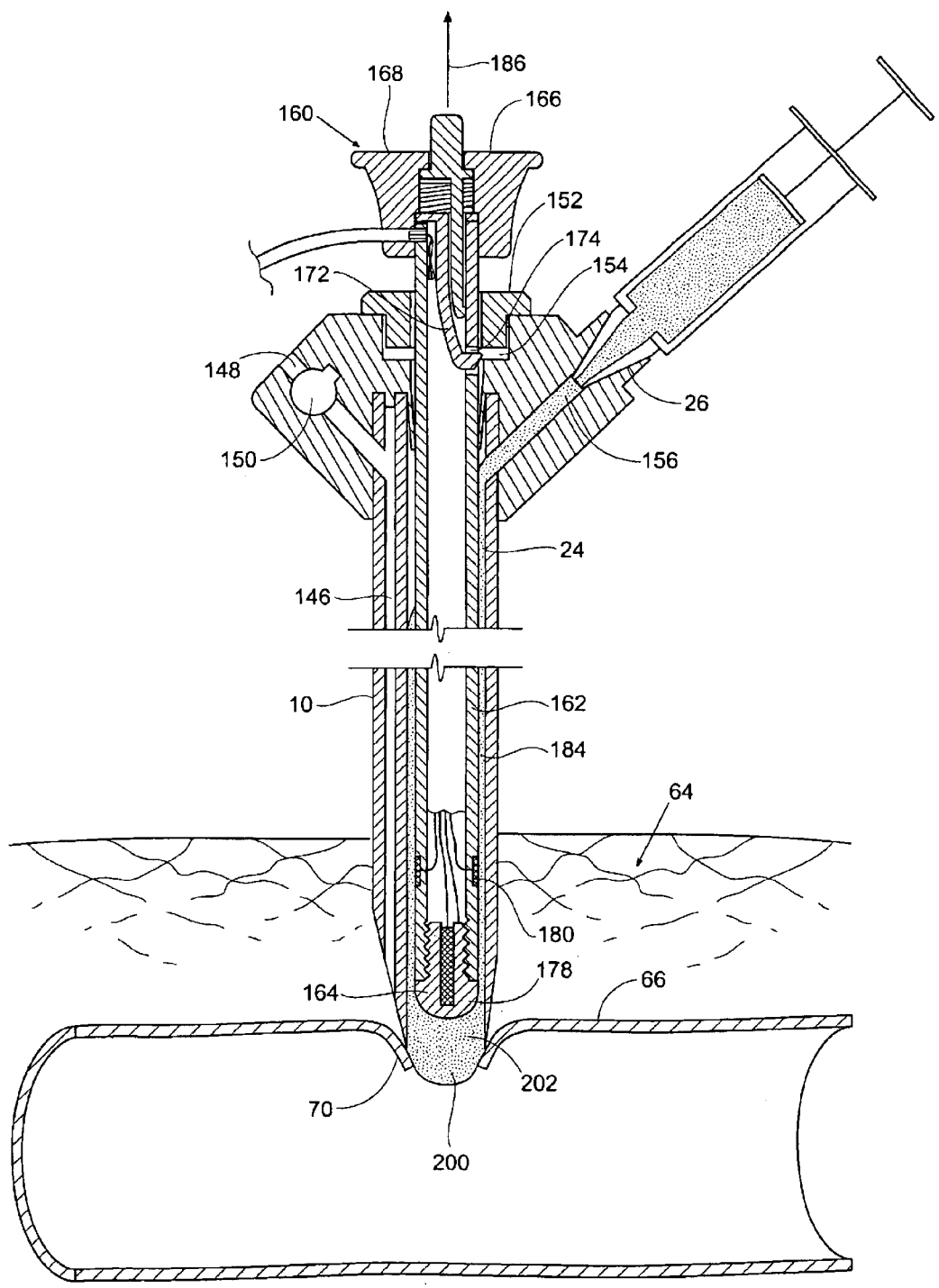
FIG. 33 illustrates closure composition delivered through a closure lumen to a puncture.

The obturator 160 is withdrawn form the device until the catch 174 engages the catch channel 154. As illustrated in FIG. 33, a gap 202 is formed between the distal end 164 of the obturator 160 and the first seal 200. A closure composition source 25 is coupled to the closure composition port 26 and closure composition 76 applied. The closure composition flows through the closure lumen and fills in the gap 202. Radiofrequency energy can be applied from the distal electrode 178 to accelerate the polymerization of the closure composition.

Figure 34:
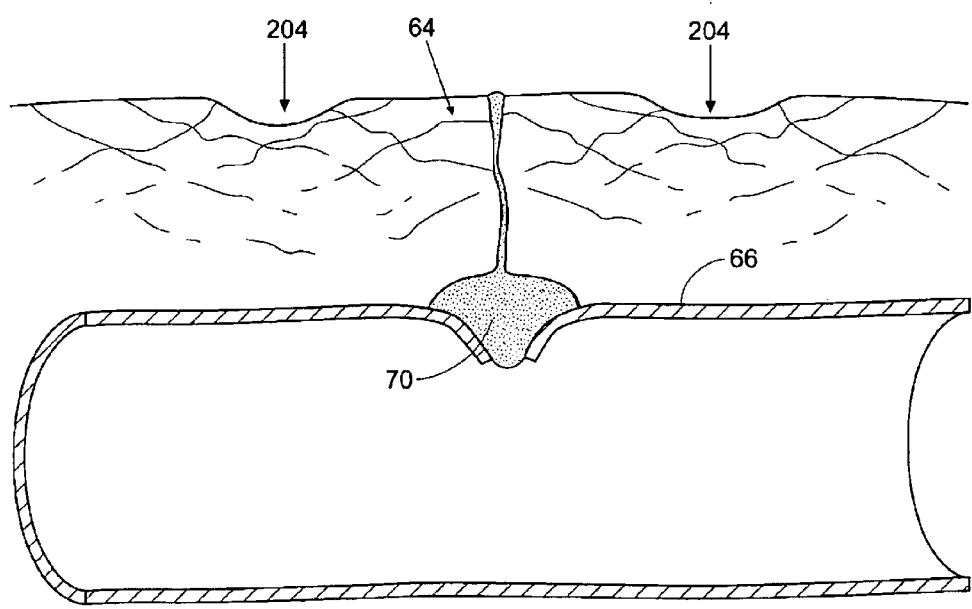
FIG. 34 is a cross section of a tissue site after closure composition has been introduced to the puncture and a closure device has been completely withdrawn from the tissue site.

FIG. 34 illustrated the tissue site 64 after the device is completely withdrawn. Pressure is applied at the arrows 204 to encourage curing of the closure composition and reduce bleeding in the tissue site 64.

The closure composition can be a fluent material that can be hydraulically translated from a reservoir through the closure lumen. When a microporous porous membrane is used, the viscosity of the closure composition should be sufficiently low that the composition can exit through pores of a microporous membrane at a reasonable rate, preferably at least about 1 mL per minute. The viscosity of the composition should also be sufficiently high that the composition will remain in the vicinity of the area to be treated with the composition for a sufficient amount of time for energy to be delivered to the composition. Energy is preferably applied for from 0.1 sec to 600 sec, more preferably for about 1 sec to about 20 sec. Accordingly, the composition should be sufficiently viscous to remain adjacent the device for these periods of time. In one embodiment, the viscosity of the fluent closure composition is between 1 cps and about 10,000 cps, preferably from about 20 cps to about 5,0000 cps.

Suitable closure compositions include, but are not limited to, closure compositions composed of three components, a matrix component, a conductivity enhancer, and a composition vehicle. Fluent closure compositions may be a homogenous solution, a slurry, a suspension, an emulsion, a colloid hydrocolloid, or a homogeneous mixture.

The matrix forming component may be any biocompatible material which can form a matrix for facilitating wound closure and sealing upon the application of a threshold energy. Examples of suitable classes of matrix forming components include proteins, glycoproteins, protoeglycans, mucosaccharides and blycoaminoglycans. The matrix forming component may include ionizable functional groups such as carboxylic acid residues, protonated amino groups, etc., that increase the compatibility of the matrix forming component with water-based vehicle solvents. The matrix forming material may also include chemical functionalities that are reactive with themselves and each other when a threshold energy is applied. Ultimately, thermal or light energy will speed these so-called "cross-linking" reactions within the matrix component and between the matrix component and tissue surfaces. Examples of such reaction chemical functionalities are carboxy groups, amino groups, thiol groups, disulfide groups, hydroxy groups, ester groups, and amide groups.

When the energy source 42 used to effect the closure is RF energy, the electrical conductivity of the fluent closure composition is preferably such that the impedance is below 200 ohms, more preferably, below 10 ohms. Because of its innate conductivity, water is the preferred base vehicle for the closure composition. Additionally, many ionic conductivity enhancers are available to allow adjustment of the overall impedance of the fluent closure composition. In one embodiment the vehicle is physiologic saline solution. In principle, an aqueous vehicle may benefit from this inclusion of a conductivity enhancer; preferred enhancers are those that occur naturally in the body, such as sodium chloride, various phosphate salts, salts of simple amino acids such as aspartic acid or glutamic acid, calcium chloride, etc. The conductivity enhancer may also function as a physiologic buffer to minimize acid or alkaline effects. The components may be a mixture of sodium and potassium salts at levels to mimic those typically found in the body.

The liquid vehicle is preferably water. Relatively inert viscosity modifiers may be included, such as polysaccharides, poly(alkylene oxides), and material gums such as carnageenan and xanthan gum. Viscosity modifier selection and level are controlled so as not to detrimentally affect the overall conductivity of the fluent closure composition if RF energy is used.

Listed in Table 1 are examples of matrix components that may be employed. Listed in Table 2 are examples of conductivity enhancers that may be employed. Listed in Table 3 are examples of composition vehicles that may be employed.

TABLE 1

Matrix Components

Proteins

- collagen, albumin, elastin, fibrin, laminin, algin, gelatin, fibronectin
- polypeptides, e.g. glutathione Saccharides

- polysaccharides, oligosaccharides, monosaccharides
- starch and derivatives, e.g. amylose, amylopectin, dextrin
- carbohydrate materials (aldo- and keto-derivatives of saccharides)

TABLE 1-continued

Matrix Components

Muco-polysaccharides

- N-hetero saccharides (polymeric, oligomeric and monomeric), preferably hexosamine derivatives
- N-substituted saccharide derivatives (polymeric, oligomeric and monomeric), preferably N-acetyl derivatives
- O-substituted saccharide derivatives, polymeric and oligomeric, preferably O-sulfato derivatives (—O—$SO_3H$ functionality), e.g., chrondoin B sulfate, a hexosamine derivative which has both N-acetylation and O-sulfonation
- Glycosaminoglycans (GAG's, linear N-hetero polysaccharides; e.g., heparin, heparan sulfate, keratosulfate, dermatan, hyaluronic acid, agarose (galactan), carrageenan)

Mucoproteins and Proteoglycans

- hexosamine-protein and saccharide-hexosamine-protein conjugates
- Chemically modified proteins, saccharides, GAG's and muco-polysaccharides
- derivatives prepared by acetylation, alkylation or sulfonation of hydroxyl, amino or carboxy functional sites, such a acetylated or sulfonated collagen
- derivatives prepared by thionylation (introducing —$SO_2$—), sulfurization (—S—), or disulfide (—SS—) coupling Synthetic Polymer Conjugates

- synthetic functional polymers covalently bonded to proteins, saccharides and muco-polysaccharides either by direct interaction, pre-functionalization of either synthetic polymer or natural material or by use of a coupling agent to bond the synthetic polymer and protein, saccharide, GAG or muco-polysaccharide together. Examples of synthetic polymers include poly(alkylene oxide)s, such as poly (ethylene oxide) (PEO), polycaprolactones, polyanhydrides, polyorthocarbonates, polyglycolides, polyactides, polydioxanones or co-polymers thereof.

TABLE 2

Conductivity Enhancing Materials

Inorganic ionic salts

- Cationic component: derived from alkaline and alkaline earth elements, preferred cation is sodium, $Na^+$
- Anionic component: halide, preferably chloride, phosphate (—O—$PO_3^{-3}$, —O—$PO_4H^{-2}$, —O—$PO_4\ H_2^{-1}$), carbonate, bicarbonate Organic ionic salts

- Cationic component: ammonium, derived from protonation of lysine or arginine residues
- Anionic component: carboxylate, e.g. asparate or glutamate, O-phosphate ester (—O—$PO_3^{-3}$, —O—$PO_4H^{-2}$, —O—$PO_4\ H_2^{-1}$), (glucose-1-phosphate, glucose- 6-phosphate, polysaccharide phosphates and polyphosphates), O-sulfate ester (e.g., glycasoaminoglycan sulfates, such as heparan sulfate, chrondoin sulfate)

TABLE 3

Composition Vehicles

Water
Water-poly(alkylene oxide) mixtures, e.g. water-poly(ethylene oxide) mixtures While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. An apparatus having a distal end, the apparatus sized and configured for introducing a catheter instrument through a vessel puncture site and introducing a closure composition to seal the vessel puncture site after removal of the catheter instrument, the apparatus comprising a unitary elongated body adapted for passage through a tissue puncture and having an end region defining the distal end of the apparatus and adapted to occupy a position adjacent the vessel puncture site, the body including a circumferential wall having an inner surface and an outer surface, a first lumen in the elongated body, the first lumen being defined by the inner surface of the circumferential wall and accommodating passage of a catheter instrument through the vessel puncture site and removal of the catheter instrument from the vessel puncture site, a closure composition comprising a combination of closure components which, when combined, react to form the closure composition, a second lumen in the elongated body separate from the first lumen and being defined by a bore within the circumferential wall between the inner and outer surfaces, the second lumen having a fluid delivery port located at a fixed distance from the distal end of the apparatus, the second lumen being adapted for introducing the closure composition to seal the vessel puncture site after removal of the catheter instrument, and one or more dispensers in fluid communication with the second lumen for dispensing the closure components as a combination that reacts in situ to form the closure composition adjacent the vessel puncture site, the first and second lumens being at least partially free of communication with each other.

2. The assembly of claim 1 wherein the closure components include a matrix component.

3. The assembly of claim 2 wherein the matrix component is a biocompatible material.

4. The assembly of claim 3 wherein the biocompatible material is selected from a group consisting essentially of proteins, saccharides, mucopolysaccharides, mucoproteins and proteoglycans, and synthetic polymer conjugates.

5. The assembly of claim 2 wherein the matrix component includes ionizable functional groups that increase compatibility of the matrix component with water-based solvents.

6. The assembly of claim 2 wherein the matrix component includes chemical functionalities that are reactive with themselves and each other.

7. The assembly of claim 6 wherein the chemical functionalities are selected from a group consisting essentially of a carboxy group, an amino group, a thiol group, a disulfide group, a hydroxy group, an ester group, and an amide group.

8. The assembly of claim 1 wherein the closure components include a conductivity enhancing material.

9. The assembly of claim 8 further including an electrode on the elongated body to conduct electrical energy through the conductivity enhancer to increase rate of formation of the closure composition.

10. The assembly of claim 8 wherein the conductivity enhancer includes physiologic saline.

11. The assembly of claim 8 wherein the conductivity enhancer functions as a physiologic buffer.

12. The assembly of claim 8 wherein the conductivity enhancer includes at least one of an inorganic ionic salt and an organic ionic salt.

13. The assembly of claim 1 wherein the closure components include a composition vehicle.

14. The assembly of claim 13 wherein the composition vehicle includes water.

15. The assembly of claim 1 wherein the closure components include a matrix component, a conductivity enhancing material, and a composition vehicle.

16. The assembly of claim 15 wherein the matrix component is a biocompatible material.

17. The assembly of claim 16 wherein the biocompatible material is selected from a group consisting essentially of proteins, saccharides, mucopolysaccharides, mucoproteins and proteoglycans, and synthetic polymer conjugates.

18. The assembly of claim 15 wherein the matrix component includes ionizable functional groups that increase compatibility of the matrix component with water-based solvents.

19. The assembly of claim 15 wherein the matrix component includes chemical functionalities that are reactive with themselves and each other.

20. The assembly of claim 19 wherein the chemical functionalities are selected from a group consisting essentially of a carboxy group, an amino group, a thiol group, a disulfide group, a hydroxy group, an ester group, and an amide group.

21. The assembly of claim 15 further including an electrode on the elongated body to conduct electrical energy through the conductivity enhancer to increase rate of formation of the closure composition.

22. The assembly of claim 15 wherein the conductivity enhancer includes physiologic saline.

23. The assembly of claim 15 wherein the conductivity enhancer functions as a physiologic buffer.

24. The assembly of claim 15 wherein the conductivity enhancer includes at least one of an inorganic ionic salt and an organic ionic salt.

25. The assembly of claim 15 wherein the composition vehicle includes water.

* * * * *

UNITED STATES PATENT AND TRADEMARK OFFICE
CERTIFICATE OF CORRECTION

PATENT NO. : 6,733,515 B1
DATED : May 11, 2004
INVENTOR(S) : Stuart D. Edwards et al.

It is certified that error appears in the above-identified patent and that said Letters Patent is hereby corrected as shown below:

Title page,
Item [56], References Cited, OTHER PUBLICATIONS, delete "Vascular Solution, Inc. Products, www.vascularsolutions.com, Information on site Nov. 12, 2003."
"Anand," reference, delete "*Medicaine*" and substitute -- *Medicine* --
"Goldstein," reference, delete "Proshesis" an substitute -- Prosthesis --
"Grubbs," reference, after "et al." delete "Enhanccement" and substitute
-- Enhancement --.
"Kopchok," reference (first occurrence), after "Tissue" delete "Rusion" and substitute
-- Fusion --.
"Kopchok," reference (second occurrence), after "welding:" delete "he" and substitute
-- the --.
"Kopchok," reference (third occurrence), after "Laser" delete "Veascular" and substitute
-- Vascular --.
"Nimni," reference, after "on" delete "he" and substitute -- the --.

Signed and Sealed this

Twenty-fourth Day of August, 2004

JON W. DUDAS
*Director of the United States Patent and Trademark Office*